United States Patent
Cohen et al.

(10) Patent No.: US 9,731,046 B2
(45) Date of Patent: Aug. 15, 2017

(54) HYDROGEL SYSTEM COMPRISING SPATIALLY SEPARATED BIOACTIVE POLYPEPTIDES

(71) Applicant: BEN-GURION UNIVERSITY OF THE NEGEV RESEARCH AND DEVELOPMENT AUTHORITY, Beer Sheva (IL)

(72) Inventors: Smadar Cohen, Beer Sheva (IL); Tali Re'Em, Tel Aviv (IL); Emil Ruvinov, Arad (IL)

(73) Assignee: Ben Gurion University of the Negev Research and Development Authority, Beer Sheva (IL)

( * ) Notice: Subject to any disclaimer, the term of this patent is extended or adjusted under 35 U.S.C. 154(b) by 0 days.

(21) Appl. No.: 14/380,161

(22) PCT Filed: Feb. 21, 2013

(86) PCT No.: PCT/IL2013/050161
§ 371 (c)(1),
(2) Date: Aug. 21, 2014

(87) PCT Pub. No.: WO2013/124855
PCT Pub. Date: Aug. 29, 2013

(65) Prior Publication Data
US 2015/0051148 A1 Feb. 19, 2015

Related U.S. Application Data

(60) Provisional application No. 61/601,220, filed on Feb. 21, 2012.

(51) Int. Cl.
| | | |
|---|---|---|
| *A61K 38/12* | (2006.01) | |
| *C07K 16/00* | (2006.01) | |
| *A61L 27/26* | (2006.01) | |
| *A61K 38/18* | (2006.01) | |
| *A61L 27/52* | (2006.01) | |
| *A61L 27/54* | (2006.01) | |
| *A61K 9/00* | (2006.01) | |

(52) U.S. Cl.
CPC ............ *A61L 27/26* (2013.01); *A61K 9/0024* (2013.01); *A61K 38/18* (2013.01); *A61K 38/1841* (2013.01); *A61K 38/1875* (2013.01); *A61L 27/52* (2013.01); *A61L 27/54* (2013.01); *A61L 2300/414* (2013.01); *A61L 2300/60* (2013.01); *A61L 2430/02* (2013.01)

(58) Field of Classification Search
None
See application file for complete search history.

(56) References Cited

U.S. PATENT DOCUMENTS

| | | |
|---|---|---|
| 4,178,361 A | 12/1979 | Cohen et al. |
| 6,388,060 B1 | 5/2002 | Guo et al. |
| 6,773,723 B1 | 8/2004 | Spiro et al. |
| 7,517,856 B2 | 4/2009 | Cohen et al. |
| 7,642,240 B2 | 1/2010 | Cohen et al. |
| 8,609,126 B2 | 12/2013 | Michal et al. |
| 8,852,637 B2 | 10/2014 | Naughton et al. |
| 2007/0081976 A1 | 4/2007 | Cohen et al. |
| 2011/0212501 A1 | 9/2011 | Yoo |

FOREIGN PATENT DOCUMENTS

| | | | |
|---|---|---|---|
| EP | 1886696 | 2/2008 | |
| WO | WO 89/12464 | 12/1989 | |
| WO | WO 99/21588 | 5/1999 | |
| WO | WO 00/64481 | 11/2000 | |
| WO | WO 01/66164 | 9/2001 | |
| WO | WO 2005/035726 | 4/2005 | |
| WO | 2007043050 A2 | 4/2007 | |
| WO | 2008082766 A2 | 7/2008 | |
| WO | WO2008/082766 A2 * | 7/2008 | ............... A61F 2/44 |
| WO | 2012113812 A1 | 8/2012 | |

OTHER PUBLICATIONS

Elisseeff et. al. (SEB Journal, 2004) vol. 18, No. 4-5, pp. Abst. 310.2).*
Elisseeff et. al. SEB Journal, 2004,vol. 18, No. 4-5, pp. Abst. 310.2.*
Re'em et al. Chrondogenesis of hMSC in affinity-bound TGF-beta scaffold. Biomaterials xxx, 2011, p. 1-11.*
Shao et al: "Evaluation of a hybrid scaffold/cell construct in repair of high-load-bearing osteochondral defects in rabbits" Biomaterials 27 pp. 1071-1080. (Aug. 2005).
Schaefer et al; "Tissue-Engineered Composites for the Repair of Large Osteochondral Defects" Arthritis & Rheumatism vol. 46, No. 9 pp. 2524-2534. (Sep. 2002).

(Continued)

*Primary Examiner* — Jeanette Lieb
(74) *Attorney, Agent, or Firm* — Mark S. Cohen; Pearl Cohen Zedek Latzer Baratz LLP

(57) ABSTRACT

The present invention provides a multi-compartment hydrogel, and a sulfated polysaccharide and at least two bioactive polypeptides capable of binding said sulfated polysaccharide, for use in repair or regeneration of a damaged tissue in a mammal. Also provided is a method for constructing the multi-compartment hydrogel. The present invention also provides a method for the repair or regeneration of a damaged tissue in a mammal, and a kit for constructing a multi-compartment hydrogel.

34 Claims, 12 Drawing Sheets

(56) References Cited

OTHER PUBLICATIONS

Nixon et al: "Enhanced Repair of Extensive Articular Defects by Insulin-like Growth Factor-I-laden Fibrin Composites" Journal of Orthopaedic Research 12 pp. 475-487. (Jul. 1999).
Marcacci et al: "Articular Cartilage Engineering with Hyalograft C—3-Year Clinical Results" Clinical Orthopaedics and Related Research No. 435, pp. 96-105. (Jun. 2005).
Gotterbarm et al: "An in vivo study of a growth-factor enhanced, cell free, two-layered collagen-tricalcium phosphate in deep osteochondral defects" Biomaterials 27 pp. 3387-3395. (Jun. 2006).
Crawford et al: "An Autologous Cartilage Tissue Implant NeoCart for Treatment of Grade III Chondral Injury to the Distal Femur" The American Journal of Sports Medicine, vol. 37, No. 7 pp. 1334-1343. (Jul. 2009).
Re'em. Tali et al. "Simultaneous regeneration of articular cartilage and subchondral bone induced by spatially presented TGF-beta and BMP-4 in a bilayer affinity binding system" Acta Biomaterialia, pp. 3283-3293, vol. 8, No. 9 (Sep. 2012).
Elisseeff, Jennifer, "Regenerating organized tissues and understanding cell-cell interactions", FASEB Journal, vol. 18, No. 4-5, (Dec. 31, 2004)—Abstract only.
Re'em. Tali et al. "Chondrogenesis of hMSC in affinity-bound TGF-beta scaffolds", Biomaterials, pp. 751-761, vol. 33, No. 3, (Jan. 3, 2012).
Esmaiel Jabbari, "Engineering Bone Formation with Peptidomimetic Hybrid Biomaterials", 31st Annual International Conference of the IEEE EMBS, pp. 1172-1175, vol. 2009, (Dec. 31, 2009).
Akashi et al. "Synthesis and anticoagulant activity of sulfated glucoside-bearing polymer" Bioconjug Chem. Jul.-Aug. 1996;7(4):393-5.
Amara et al. "Stromal cell-derived factor-1alpha associates with heparan sulfates through the first beta-strand of the chemokine" J Biol Chem. Aug. 20, 1999;274(34):23916-25.
Capila et al. "Heparin-protein interactions" Angewandte Chemie International Edition. Feb. 1, 2002;41(3):390-412.
Cochran et al. "Probing the interactions of phosphosulfomannans with angiogenic growth factors by surface plasmon resonance" J Med Chem. Oct. 9, 2003;46(21):4601-8.
Cohen et al. "Direct freeform fabrication of seeded hydrogels in arbitrary geometries" Tissue Eng. May 2006;12(5):1325-35.
Dodgson et al. "A note on the determination of the ester sulphate content of sulphated polysaccharides" Biochem J. Jul. 1962;84:106-10.
Dvir et al. "Prevascularization of cardiac patch on the omentum improves its therapeutic outcome" Proc Natl Acad Sci U S A. Sep. 1, 2009;106(35):14990-5.
Freeman et al. "The effect of sulfation of alginate hydrogels on the specific binding and controlled release of heparin-binding proteins" Biomaterials. Aug. 2008;29(22):3260-8.
Freeman et al. "Abstract Book of the Joint Meeting of the Tissue Engineering Society International and the European Tissue Engineering Society", Oct. 13, 2004, XP007923141.
Freeman et al. "The influence of the sequential delivery of angiogenic factors from affinity-binding alginate scaffolds on vascularization" Biomaterials. Apr. 2009;30(11):2122-31.
Geresh et al. "Sulfation of extracellular polysaccharides of red microalgae: preparation, characterization and propert" J Biochem Biophys Methods. Jan. 4, 2002;50(2-3):179-87.
Goretzki et al. "High-affinity binding of basic fibroblast growth factor and platelet-derived growth factor-AA to the core protein of the NG2 proteoglycan" J Biol Chem. Jun. 11, 1999;274(24):16831-7.
Habuchi et al. "Structure of a heparan sulphate oligosaccharide that binds to basic fibroblast growth factor" Biochem J. Aug. 1, 1992;285 ( Pt 3):805-13.
"Iduronic Acid"; downloaded from: en.wikipedia.org/wiki/Iduronic_acid.
Kamei et al. "The analysis of heparin-protein interactions using evanescent wave biosensor with regioselectively desulfated heparins as the ligands" Anal Biochem. Aug. 15, 2001;295(2):203-13.
Karp et al. "Mesenchymal stem cell homing: the devil is in the details" Cell Stem Mar. 6, 2009;4(3):206-16.
Kock et al. "Tissue engineering of functional articular cartilage: the current status" Cell Tissue Res. Mar. 2012;347(3):613-27.
Kohan et al. "Osteopontin induces airway remodeling and lung fibroblast activation in a murine model of asthma" Am J Respir Cell Mol Biol. Sep. 2009;41(3):290-6.
Kozawa et al. "Divergent regulation by p44/p42 Map kinase and p38 MAP kinase of bone morphogenetic protein-4-stimulated osteocalcin synthesis in osteoblasts" J Cell Biochem. 2002;84(3):583-9.
Kreuger et al. Characterization of fibroblast growth factor 1 binding heparan sulfate domain Glycobiology. Jul. 1999;9(7):723-9.
Laird et al. "Stem cell trafficking in tissue development, growth, and disease" Cell. Feb. 22, 2008;132(4):612-30.
Lang et al. "Tamarind seed polysaccharide: preparation, characterisation and solution properties of carboxylated, sulphated and alkylaminated derivatives". Carbohydrate polymers. Dec. 31, 1992;17(3):185-98.
Levy et al. "Signal transducer and activator of transcription 3-A key molecular switch for human mesenchymal stem cell proliferation" Int J Biochem Cell Biol. 2008;40(11):2606-18.
Levy et al. "Highly efficient osteogenic differentiation of human mesenchymal stem cells by eradication of STAT3 signaling" Int J Biochem Cell Biol. Nov. 2010;42(11):1823-30.
Ng et al. "Zonal chondrocytes seeded in a layered agarose hydrogel create engineered cartilage with depth-dependent cellular and mechanical inhomogeneity" Tissue Eng Part A. Sep. 2009;15(9):2315-24.
Paredes et al. "Mechanisms responsible for catalysis of the inhibition of factor Xa or thrombin by antithrombin using a covalent antithrombin-heparin complex" J Biol Chem. Jun. 27, 2003;278(26):23398-409.
Polyak et al. "Synthesis and characterization of a biotin-alginate conjugate and its application in a biosensor construction" Biomacromolecules. Mar.-Apr. 2004;5(2):389-96.
Prockop "Repair of tissues by adult stem/progenitor cells (MSCs): controversies, myths and changing paradigms" Mol Ther. Jun. 2009;17(6):939-46.
Qi et al. "Identification of genes responsible for osteoblast differentiation from human mesodermal progenitor cells" Proc Natl Acad Sci U S A. Mar. 18, 2003;100(6):3305-10.
Rahmoune et al. "Hepatocyte growth factor/scatter factor has distinct classes of binding site in heparan sulfate from mammary cells" Biochemistry. Apr. 28, 1998;37(17):6003-8.
Ruvinov et al. "The effects of controlled HGF delivery from an affinity-binding alginate biomaterial on angiogenesis and blood perfusion in a hindlimb ischemia model" Biomaterials. Jun. 2010;31(16):4573-82.
Ruvinov et al. "The promotion of myocardial repair by the sequential delivery of IGF-1 and HGF from an injectable alginate biomaterial in a model of acute myocardial infarction" Biomaterials. Jan. 2011;32(2):565-78.
Schroeder-Tefft et al. "Collagen and Heparin Matrices for Growth Factor Delivery" Journal of Controlled Release, vol. 48, 1997, pp. 29-33, XP002088404.
Shapiro et al. "Novel alginate sponges for cell culture and transplantation" Biomaterials. Apr. 1997;18(8):583-90.
Song et al. "Overlap of IGF- and heparin-binding sites in rat IGF-binding protein-5" J Mol Endocrinol. Feb. 2000;24(1):43-51.
Supplementary European Search Report for European Application No. 13752115.9 dated Oct. 1, 2015.
Wijelath et al. "Novel vascular endothelial growth factor binding domains of fibronectin enhance vascular endothelial growth factor biological activity" Circ Res. Jul. 12, 2002;91(1):25-31.
Wu et al. "Surface plasmon resonance analysis to evaluate the importance of heparin sulfate groups' binding with human aFGF and bFGF" J Zhejiang Univ Sci. Jan.-Feb. 2003;4(1):86-94.

(56) References Cited

OTHER PUBLICATIONS

Zhang et al. "A highly stable covalent conjugated heparin biochip for heparin-protein interaction studies" Anal Biochem. May 15, 2002;304(2):271-3.

* cited by examiner

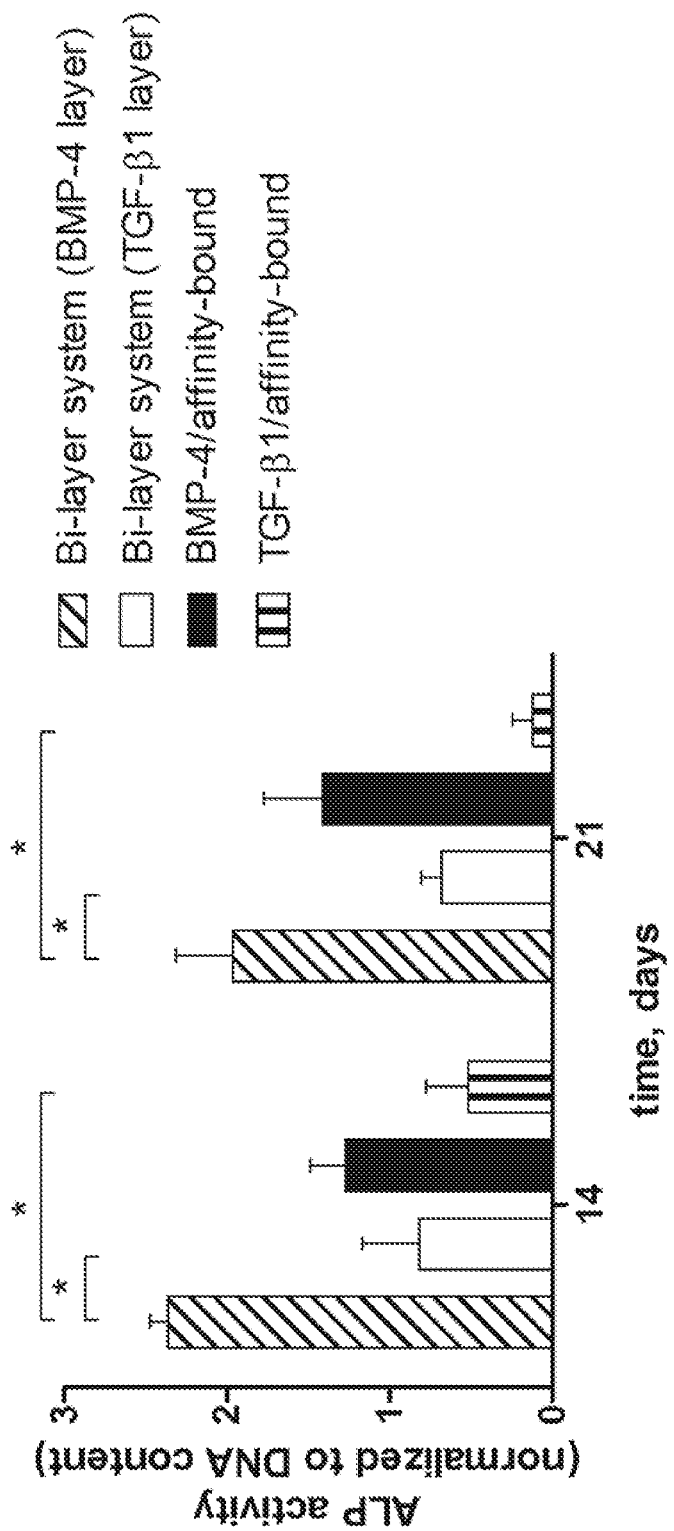

2 weeks 4 weeks

HYDROGEL SYSTEM COMPRISING SPATIALLY SEPARATED BIOACTIVE POLYPEPTIDES

TECHNICAL FIELD

The present invention relates in general to a multi-compartment hydrogel system comprising spatially separated bioactive polypeptides and its use in regeneration of complex tissue.

BACKGROUND ART

A subchondral defect is usually characterized by a structural breakdown of the articular cartilage and the bone underneath due to trauma or disease, leading to chronic disabilities. Treating such defects is an important regenerative medicine target since damaged cartilage cannot spontaneously heal itself in adults. The avascular cartilage with its dense extracellular matrix prevents chondro-progenitors from migrating to the injury site, thus greatly reducing the tissue's regenerative potential. For decades, cell-based strategies have been developed for treating cartilage defects, by injecting cell suspensions (chondrocytes, stem cells) or their combination with biomaterials (Marcacci M. et al., 2005, Crawford D C. et al., 2009). These strategies have encountered crucial barriers in therapeutic translation, due to concerns with the cells in use (e.g., rejection, pathogen contaminants, tumorigenesis) and technical issues (packaging, storage, shipping) as well as difficulties in clinical adoption and regulatory approval (Prockop D J. et al., 2009).

Nowadays, following the identification and efficient production of molecular inducers of tissue regeneration and with the development of hydrogels for their sustained delivery, there is a shift in trend towards adopting acellular therapeutic approaches. Such strategies have been fueled by the finding that micro-fracture surgical techniques can induce the recruitment of bone marrow stem cells into the chondral defect and initiate its repair. To enhance endogenous cell recruitment, combinations of molecular inducers and biomaterials to prolong factor activity, have been applied (Nixon A J, et al., 1999, Gotterbarm T. et al., 2006). These strategies for repairing osteochondral defects are still in their infancy and are considered to be provocative, and in need of additional testing (Laird D J. et al., 2008, Karp J M. et al., 2009).

WO 2007/043050, one inventor of which is a co-inventor of the present invention, provides bioconjugates comprising a sulfated polysaccharide such as alginate sulfate and hyaluronan sulfate and at least one bioactive polypeptide capable of binding a sulfate group of said sulfated polysaccharide. The bioactive polypeptide can be a heparin-binding polypeptide or a positively-charged polypeptide and is preferably a peptide growth factor or a cytokine. The bioconjugates serve as delivery systems for sustained release of the bioactive polypeptides.

Affinity binding of TGF-$\beta$1 to alginate-sulfate/alginate scaffold was recently disclosed (Re'em et al., 2012), demonstrating that such binding maintained the factor's activity, enabled its sustained release and promoted human mesenchymal stem cell differentiation towards committed chondrocyte.

SUMMARY OF INVENTION

In one aspect, the present invention provides a multi-compartment hydrogel for use in repair or regeneration of a damaged tissue in a mammal, said multi-compartment hydrogel being obtained by a method comprising the steps of (i) mixing a sulfated polysaccharide and at least one bioactive polypeptide capable of binding said sulfated polysaccharide, thereby forming a bioconjugate; (ii) mixing said bioconjugate of (i) with a material capable of forming a hydrogel, thereby forming a composite material comprising the bioconjugate; (iii) applying said composite material comprising the bioconjugate of (ii) to a scaffold comprising a void or a wound in a damaged tissue in the mammal and optionally adding a hydrogel inducer, thereby forming a hydrogel compartment in said scaffold; and (iv) repeating steps (i) to (iii) until the desired number of hydrogel compartments is obtained, wherein each time that step (i) is repeated, the bioconjugate formed in (i) comprises at least one different bioactive peptide and is therefore distinct from the previously obtained bioconjugate, and each new hydrogel compartment formed in (iii) is in contact with and is physically connected to at least one of the previously formed hydrogel compartments.

In another aspect, the present invention provides a method for constructing a multi-compartment hydrogel, comprising the steps of (i) mixing a sulfated polysaccharide and at least one bioactive polypeptide capable of binding said sulfated polysaccharide, thereby forming a bioconjugate; (ii) mixing said bioconjugate of (i) with a material capable of forming a hydrogel, thereby forming a composite material comprising the bioconjugate; (iii) applying said composite material comprising the bioconjugate of (ii) to a scaffold and optionally adding a hydrogel inducer, thereby forming a hydrogel compartment in said scaffold; and (iv) repeating steps (i) to (iii) until the desired number of hydrogel compartments is obtained, wherein each time that step (i) is repeated, the bioconjugate formed in (i) comprises at least one different bioactive peptide and is therefore distinct from each one of the previously obtained bioconjugates, and each new hydrogel compartment formed in (iii) is in contact with at least one of the previously formed hydrogel compartments, thereby forming a multi-compartment hydrogel in said scaffold.

In still another aspect, the present invention provides a multi-compartment hydrogel obtained by the method as defined above.

In yet another aspect, the present invention provides a method for the repair or regeneration of a damaged tissue in a mammal, comprising implanting a multi-compartment hydrogel in a void in said tissue.

In a further aspect, the present invention provides a kit for use in repair or regeneration of a damaged tissue in a mammal, wherein said kit comprises components for constructing a multi-compartment hydrogel, wherein each compartment comprises a bioconjugate comprising a sulfated polysaccharide and at least one different bioactive peptide, said bioconjugate is therefore distinct from each one of the other bioconjugates, and each hydrogel compartment is in contact with at least one of the other hydrogel compartments, said kit comprising (i) containers comprising components for forming at least two bioconjugates, wherein said components comprises a sulfated polysaccharide and at least two bioactive polypeptides capable of binding said sulfated polysaccharide; (ii) a container comprising a material capable of forming a hydrogel; (iii) optionally a scaffold; (iv) optionally a container comprising a hydrogel inducer; and (v) instructions for constructing a multi-compartment hydrogel in a scaffold according to the method of the present invention as defined herein.

BRIEF DESCRIPTION OF DRAWINGS

FIGS. 6A-B illustrate osteochondral differentiation of human mesenchymal stem cells (hMSCs) seeded in a bi-layer system, in vitro. (A) Alkaline phosphatase (ALP) activity in the BMP-4 and TGF-β1 layers in a bi-layer system, *p<0.05 (Bonferroni post-test, 2-way ANOVA). For comparison, the levels measured in a single factor system are presented. (B) Immunostaining of thin sections (5 μm) obtained from the different layers in the bi-layer system, after three weeks of hMSC cultivation, for collagen type II (see dashed ellipse) and aggrecan (see arrows)—markers for cartilage extracellular matrix (ECM), and von Kossa staining for mineralized bone matrix (see black stain). (Bar: 50 μm).

DETAILED DESCRIPTION OF THE INVENTION

Figure 1:
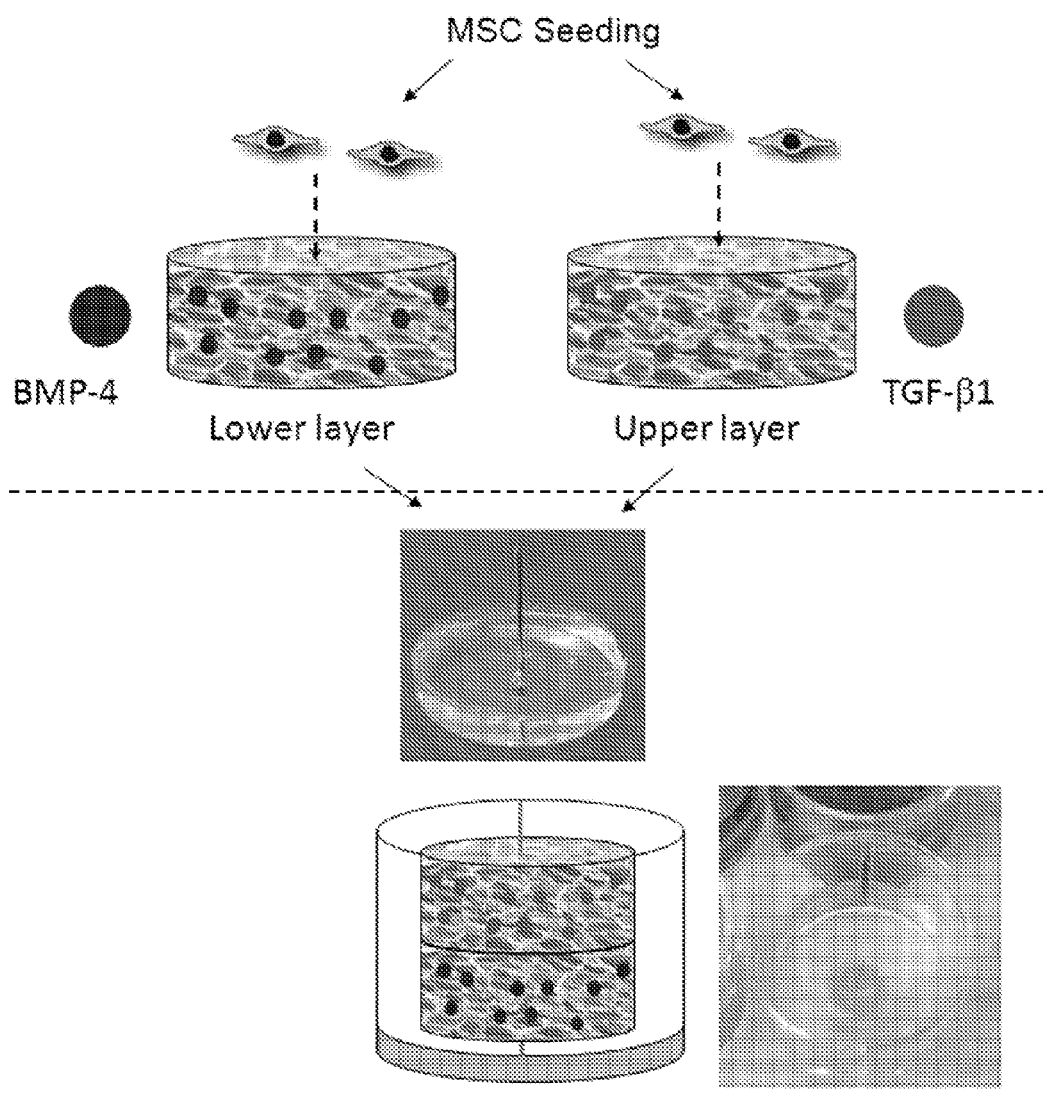
FIG. 1 depicts a scheme describing the construction of the bi-layer affinity-binding alginate scaffold. TGF-$\beta$1 and BMP-4 were affinity-bound to alginate-sulfate in macroporous alginate scaffolds. After cell seeding and a short culture of 2 days (above the dashed line), the seeded scaffolds were combined together by their assembly on a stainless steel pin placed perpendicular to a supporting polydimethylsiloxane (PDMS) layer (below the dashed line).

It has previously been shown by the inventors that when TGF-β1 is attached to a matrix via affinity interactions with alginate sulfate, its loading was significantly greater and its initial release from the scaffold was attenuated compared to its burst release (>90%) from scaffolds lacking alginate-sulfate. Such presentation of TGF-β1 led to human mesenchymal stem cells (hMSCs) chondrogenic differentiation (Re'em et al., 2012).

It is has now been found in accordance with the present invention that the osteo-inductive bone morphogenetic protein-4 (BMP-4) binds in a strong and specific manner to alginate-sulfate; and that BMP-4 bioactivity is retained when it is bound to alginate-sulfate (see Example 1). For example, MAPK signal-transduction pathway was induced in hMSCs cultured within affinity-binding scaffolds comprising BMP-4 and alginate-sulfate and osteogenic differentiation of the hMSCs was induced within the BMP-4/affinity-bound scaffold (Examples 2 and 3).

The inventors further decided to assess whether it would be possible to induce two different differentiation pathways in spatially distinct areas of a tissue, by applying to the tissue two different bioactive polypeptides wherein each polypeptide is affinity bound to separate compartments of a scaffold. Indeed, collective results according to the present invention from in vitro culture studies using seeded hMSCs in a two-layer scaffold, as well as from rabbit and pig subchondral defects, where an acellular two-layer hydrogel was created in-situ, demonstrate the unique ability of the bi-layer system to regenerate distinguishable cartilage and bone in their respective layers, thus re-creating the osteochondral interface (Examples 4 to 9).

The key attribute to the success of the bi-layer system may be the presentation of the inducible factors as affinity-bound to the matrix, mimicking their presentation by the extracellular matrix (ECM). This was attained according to the present invention by incorporating alginate-sulfate into the hydrogel, enabling the affinity binding of BMP-4 and TGF-β1 at concentration loadings found previously to be efficient to induce cell differentiation. The prolonged presentation and activity of the factors induced the complete differentiation of hMSCs to chondrocytes and osteoblasts, depending on the type of inducible factor in use (Re'em et al., 2012; Examples 2 and 3). When combined in vitro into a bi-layer system presenting TGF-β1 in one layer and BMP-4 in a second layer, seeded hMSCs differentiated and formed cartilage and bone in their respective layers within 3 weeks. In the TGF-β1 layer, but not in the BMP-4 layer, type II collagen and aggrecan, typical cartilaginous components, were abundant. Significantly greater levels of alkaline phosphatase activity and increased mineralized bone matrix deposition were observed in the BMP-4 layer (Example 4). The simultaneous differentiation of hMSCs in the two layers confirmed the factor's spatial presentation and its local action on cells in the bi-layer system; thus implying that there was minimal cross-diffusion of the growth factors to the adjacent layers.

In a rabbit model of subchondral defect, in situ reconstruction of the two-layer hydrogel, with factor-loading similar to the amount found effective in inducing cell differentiation in vitro is shown herein to induce endogenous regeneration of cartilage and subchondral bone underneath, as judged by microcomputer-tomography (μCT) scans and histological and immunostaining for collagen type II analyses. Four weeks after implantation, the drilled hole was completely filled by a distinguishable cartilage layer with woven bone underneath. Since no cells were co-injected with the hydrogel, it is assumed that alginate hydrogel enabled the penetration of migrating cells from the bone marrow that were coaxed to differentiate either to chondrocytes or bone cells, depending on the layer to which they migrated, thus creating the osteochondral interface. The progression in migrated cell differentiation along the endochondral bone formation is notably demonstrated when comparing the results of the 2-week explants to those after 4 weeks. With time, the number of chondrocytes in the superficial cartilage layer has increased concomitantly with the enhanced cartilage ECM deposition of proteoglycans and collagen type II. The chondrocytes were evenly distributed, isolated from each other by the cartilaginous ECM, and no mineralization was noted, suggesting that the newly-formed cartilage would be able to sustain the appropriate physiological load. In the deeper layer, pre-hypertrophic chondrocytes, noted after 2 weeks by the flattened, elongated morphology and depositions of proteoglycans and collagen type II, were replaced after 4 weeks by large hypertrophic cells organized in columnar structures. The deeper layer eventually formed the woven bone as detected by μCT analysis.

The bi-layer system described herein is unique partially since it presents the factors in a similar manner to their natural presentation by the ECM, as affinity-bound to the matrix. Moreover, since the hydrogel is formed in situ, it may be delivered via a minimally-invasive method and its final shape will accurately match that of the irregular formed subchondral defect, ensuring a precise fit between the biomaterial and the defected tissue, and thus enabling its better integration with the surrounding tissues. The proposed system is an attractive solution, better applicable than strategies which require press-fit fixation of a pre-formed material (Gotterbarm T et al., 2006, Schaefer D et al., 2002, Shao X X et al., 2006), or cellular strategies which suffer from the inherent disadvantages detailed herein. Partial or complete regeneration of the missing or damaged tissue can be obtained, both in terms of location (within the void of the damaged tissue) and type (the nature of the regenerated tissue can be manipulated by incorporating the growth factor relevant for regeneration of the damaged tissue).

Thus, in one aspect the present invention provides a multi-compartment hydrogel for use in repair or regeneration of a damaged tissue in a mammal, said multi-compartment hydrogel being obtained by a method comprising the steps of (i) mixing a sulfated polysaccharide and at least one bioactive polypeptide capable of binding said sulfated polysaccharide, thereby forming a bioconjugate; (ii) mixing said bioconjugate of (i) with a material capable of forming a hydrogel, thereby forming a composite material comprising the bioconjugate; (iii) applying said composite material comprising the bioconjugate of (ii) to a scaffold comprising a void or a wound in a damaged tissue in the mammal and optionally adding a hydrogel inducer, thereby forming a hydrogel compartment in said scaffold; and (iv) repeating steps (i) to (iii) until the desired number of hydrogel compartments is obtained, wherein each time that step (i) is repeated, the bioconjugate formed in (i) comprises at least one different bioactive peptide and is therefore distinct from the previously obtained bioconjugate, and each new hydrogel compartment formed in (iii) is in contact with and is physically connected to at least one of the previously formed hydrogel compartments.

The multi-compartment hydrogel of the present invention is preferably constructed in situ inside the wounded tissue; however, in certain cases there are also advantages in preforming the multi-compartment hydrogel using a mold that confers a desired three dimensional structure to the multi-compartment hydrogel that resembles the wound or cavity into which it is to be press-fixed. The present invention provides solutions for both techniques.

Thus, in another aspect, the present invention provides a method for constructing a multi-compartment hydrogel, comprising the steps of (i) mixing a sulfated polysaccharide and at least one bioactive polypeptide capable of binding said sulfated polysaccharide, thereby forming a bioconjugate; (ii) mixing said bioconjugate of (i) with a material capable of forming a hydrogel, thereby forming a composite material comprising the bioconjugate; (iii) applying said composite material comprising the bioconjugate of (ii) to a scaffold and optionally adding a hydrogel inducer, thereby forming a hydrogel compartment in said scaffold; and (iv) repeating steps (i) to (iii) until the desired number of hydrogel compartments is obtained, wherein each time that step (i) is repeated, the bioconjugate formed in (i) comprises at least one different bioactive peptide and is therefore distinct from each one of the previously obtained bioconjugates, and each new hydrogel compartment formed in (iii) is in contact with at least one of the previously formed hydrogel compartments, thereby forming a multi-compartment hydrogel in said scaffold.

In another aspect, the present invention provides a multi-compartment hydrogel obtained by the method as defined herein above.

In yet another aspect, the present invention provides methods for the repair or regeneration of a damaged tissue in a mammal, such as regeneration of articular cartilage and/or woven bone and repair of subchondral defects, the method comprising the steps of (i) mixing a sulfated polysaccharide and at least one bioactive polypeptide capable of binding said sulfated polysaccharide, thereby forming a bioconjugate; (ii) mixing said bioconjugate of (i) with a material capable of forming a hydrogel, thereby forming a composite material comprising the bioconjugate; (iii) applying said composite material comprising the bioconjugate of (ii) to a void or a wound in a damaged tissue in the mammal and optionally adding a hydrogel inducer, thereby forming a hydrogel compartment in said scaffold; and (iv) repeating steps (i) to (iii) until the desired number of hydrogel compartments is obtained, wherein each time that step (i) is repeated, the bioconjugate formed in (i) comprises at least one different bioactive peptide and is therefore distinct from the previously obtained bioconjugate, and each new hydrogel compartment formed in (iii) is in contact with and is physically connected to at least one of the previously formed hydrogel compartments.

In another aspect the present invention provides a method for the repair or regeneration of a damaged tissue in a mammal, comprising implanting a multi-compartment hydrogel of the present invention in a void in said tissue.

In yet another aspect the present invention provides a kit for use in repair or regeneration of a damaged tissue in a mammal, wherein said kit comprises components for constructing a multi-compartment hydrogel, wherein each compartment comprises a bioconjugate comprising a sulfated polysaccharide and at least one different bioactive peptide, said bioconjugate is therefore distinct from each one of the other bioconjugates, and each hydrogel compartment is in contact with at least one of the other hydrogel compartments, said kit comprising (i) containers comprising components for forming at least two bioconjugates, wherein said components comprises a sulfated polysaccharide and at least two bioactive polypeptides capable of binding said sulfated polysaccharide; (ii) a container comprising a material capable of forming a hydrogel; (iii) optionally a scaffold; (iv) optionally a container comprising a hydrogel inducer; and (v) instructions for constructing a multi-compartment hydrogel in a scaffold according to the method according to the present invention as defined herein.

The term "compartment" as used herein refers to one of the parts or spaces into which a volume is subdivided, different in composition from its surroundings. An example of such a compartment is a solidified hydrogel unit that differs from neighboring compartments at least by the composition of bioconjugates.

The term "hydrogel" as used herein refers to a network of natural or synthetic hydrophilic polymer chains able to contain water. Examples of compounds able to form such networks are alginate, a partially calcium cross-linked alginate solution, chitosan and viscous hyaluronan.

Alginate is a polysaccharide derived from brown seaweed. It is an anionic polysaccharide composed of uronic acids (guluronic (G) and mannuronic (M) acids) that undergoes gelation in the presence of bivalent cations, such as $Ca^{2+}$ and $Ba^{2+}$. In the pharmaceutical/medicinal fields, it is used successfully as encapsulation material, mostly for cells (bacterial, plant and mammalian cells). For molecules, it is much less effective, and even macromolecules in size of 250 kDa are rapidly released from alginate hydrogel systems. In particular, biological molecules of interest such as cytokines, growth factors, with sizes ranging between 5 to 100 kDa, are rapidly released.

The term "repair" as used herein refers to partial or full restoration of structural damage of a tissue or organ to sound structural and/or functional condition, wherein the damage is caused to the tissue or organ by an insult. The term "regeneration" as used herein refers to the ability to recreate lost, missing or damaged tissues For example, repair or regeneration of a subchondral defect comprises partial or complete reconstitution of articular cartilage and the bone underneath and/or partial or complete reconstitution of movement of the damaged joint.

Articular cartilage is a highly organized avascular tissue composed of chondrocytes embedded within an extracellular matrix of collagens, proteoglycans and non-collagenous proteins. Its primary function is to enable the smooth articulation of joint surfaces, and to cushion compressive, tensile and shearing forces.

Non-limiting examples of insults to a tissue that cause damage are trauma, disease or disorder, friction, continuous friction, shearing stresses and combinations thereof. Trauma is commonly caused by sport-related injuries. Traumatic cartilage injuries can generally be categorized as microdamage or blunt trauma, chondral fractures and osteochondral fractures. One non-limiting example of a disease that may cause subchondral defects is osteoarthritis, which primarily targets the cartilage, but which as a secondary insult also affects the subchondral bone. Also diseases that primarily targets the subchondral bone may cause subchondral defects, such as osteochondritis and osteonecrosis. In these cases, the damaged bone eventually causes the collapse and degeneration of the overlying cartilage. Ischemia, subsequent necrosis and possibly genetics are etiologic factors in non-traumatic damage.

The term "bioconjugate" as used herein refers to a sulfated polysaccharide bound covalently or non-covalently to a bioactive polypeptide. Examples of non-covalent binding are binding involving ionic bonds, electrostatic interactions, hydrophobic interactions, hydrogen bonds or van der Waals forces.

The term "bioactive polypeptide" as used herein refers to a polypeptide exhibiting a variety of pharmacological activities in vivo and include, without being limited to, growth factors, cytokines, chemokines, angiogenic factors, immunomodulators, hormones, and the like.

In the present application, the terms "polypeptide" and "proteins" are used interchangeably.

The term "hydrogel inducer" as used herein refers to any compound able to initiate and/or solidify a hydrogel formation. It is clear that different hydrogels require different inducers for polymerization. For example, alginate-based hydrogels, in which alginate units are not covalently linked to each other, require a divalent cation, such as $Be^{+2}$, $Mg^{+2}$ or $Ca^{+2}$, preferably $Ca^{+2}$, for chelation-based polymerization. On the other hand, chitosan and viscous hyaluronan, which are covalently linked during hydrogel formation, require different inducers, known in the field.

In certain embodiments, the sulfated polysaccharide comprises uronic acid residues such D-glucuronic, D-galacturonic, D-mannuronic, L-iduronic, and L-guluronic acids. Examples of polysaccharides comprising uronic acid residues include, but are not limited to, alginic acid salts, preferably sodium alginate, pectin, gums and mucilages from plant sources; and glycosaminoglycans (GAGs) from animal sources including hyaluronic acid (hyaluronan). The sulfated polysaccharides comprising uronic acid can be chemically sulfated or may be naturally sulfated polysaccharides.

In another embodiment of the present invention, the sulfated polysaccharide in the bioconjugate is alginate sulfate. In another embodiment the sulfated polysaccharide is hyaluronan sulfate.

In certain embodiments, the bioactive polypeptide is a positively-charged polypeptide and/or a heparin-binding polypeptide.

The term "heparin-binding protein or polypeptide" refers to proteins that have clusters of positively-charged basic amino acids and form ion pairs with specially defined negatively-charged sulfo or carboxyl groups on the heparin chain (Capila and Linhardt, 2002). Examples of heparin-binding proteins include, but are not limited to, thrombopoietin (TPO); proteases/esterases such as antithrombin III (AT III), serine protease inhibitor (SLP1), C1 esterase inhibitor (C1 INH) and Vaccinia virus complement control protein (VCP); growth factors such as a fibroblast growth factor (FGF, aFGF, bFGF), a FGF receptor, vascular endothelial growth factor (VEGF), insulin-like growth factor (IGF), hepatocyte growth factor (HGF), transforming growth factor β1 (TGF-β1), a platelet-derived growth factor (PDGF, PDGF-AA and PDGF-BB), and epidermal growth factor (EGF); chemokines such as platelet factor 4 (PF-4, now called CXC chemokine ligand 4 or CXCL4), stromal cell-derived factor-1 (SDF-1), IL-6, IL-8, RANTES (Regulated on Activation, Normal T Expressed and Secreted), monocyte chemoattractant protein-1 (MCP-1), macrophage inflammatory peptide-1 (MIP-1), lymphotactin, and fractalkine; lipid or membrane-binding proteins such as an annexin, apolipoprotein E (ApoE); pathogen proteins such as human immunodeficiency virus type-1 (HIV-1) coat proteins e.g. HIV-1 gp120, cyclophilin A (CypA), Tat protein, viral coat glycoprotein gC, gB or gD of herpes simplex virus (HSV), an envelope protein of Dengue virus, circumsporozoite (CS) protein of Plasmodium falciparum, bacterial surface adhesion protein OpaA; and adhesion proteins such as 1- and P-selectin, heparin-binding growth-associated molecule (HB-GAM), thrombospondin type I repeat (TSR), and amyloid P (AP).

The term "positively charged polypeptide" refers to a polypeptide/protein that has a positive net charge at physiological pH of about pH=7.5. Examples of positively charged proteins include, but are not limited to, insulin, glatiramer acetate (also known as Copolymer 1 or Cop 1), antithrombin III, interferon (IFN)-γ (also known as heparin-binding protein), IGF, somatostatin, erythropoietin, luteinizing hormone-releasing hormone (LH-RH) and interleukins such as IL-2 and IL-6.

In particular such embodiments, the bioactive polypeptide is selected from TGFβ1; a BMP such as BMP-2, 4 or 7; aFGF; PDGF-BB; PDGF-AA; VEGF; IL-6; TPO; SDF; HGF; EGF; IGF; bFGF or VEGF In certain embodiments, the binding between the bioactive polypeptide and the sulfated polysaccharide is selected from reversible non-covalent binding involving ionic bonds, electrostatic interactions, hydrophobic interactions, hydrogen bonds or van der Waals forces.

It should be understood that by having a positive charge, the bioactive polypeptides may be reversibly and un-covalently bound to the sulfated polysaccharides, which carry a negative charge due to their sulfur group. Furthermore, the high-affinity interaction between the at least one different bioactive polypeptide and the sulfated polysaccharide, enables the confinement of the at least one different bioactive polypeptide to a separate hydrogel compartment, and prevents or minimizes the unwanted diffusion of the bioactive polypeptides into other compartments.

The term "scaffold" as used herein refers to any synthetic or organic structure comprising a void. Non-limiting examples of such scaffolds are molds, casts and voids in damaged tissue in a mammal.

In certain embodiments, the scaffold is a void in a damaged tissue in a mammal. In particular, the void may be fractured or cracked bone or cartilage, cavities in bone or teeth or wounds. It should be understood that such a void can be manipulated before, during and after hydrogel deposition, for example by enlarging a cavity to enable or improve injection of the composite material.

In other certain embodiments, the scaffold is a synthetic or artificial mold.

The phrase "synthetic or artificial mold" as used herein refers to any man-made mold or cast, preferably designed to mimic, at least in part, a scaffold, i.e. a hole, wound or a void found in damaged tissues.

In certain embodiments, the material capable of forming a hydrogel is selected from alginate, a partially calcium cross-linked alginate solution, chitosan or viscous hyaluronan.

In certain embodiments, the multi-compartment hydrogel allows migration and penetration of cells into the multi-compartment hydrogel and interaction of the cells with said bioactive polypeptide.

It should be understood that in order to initiate or accelerate tissue formation in a wounded tissue, one or more compartments within the multi-compartment hydrogel may comprise one or more types of stem cells, which would reduce the need for stem cell migration from tissues surrounding the wound into the multi-compartment hydrogel. The provision of stem cells within the multi-compartment hydrogel is specifically required when the surrounding tissues have a poor endogenous stem cell population. The stem cells may be embryonic stem cells, induced pluripotent stem cells, or taken from umbilical cord or may be derived from bone marrow, adipose tissue or blood.

In certain embodiments, step (ii) in the method described above for constructing a multi-compartment hydrogel of the present invention further comprises mixing said bioconjugate of step (i) and said material capable of forming a hydrogel with stem cells, thereby forming a composite material comprising the bioconjugate and stem cells.

Thus, in certain embodiments, at least one compartment in the multi-compartment hydrogel comprises stem cells. The stem cells may be embryonic stem cells, induced pluripotent stem cells, or taken from umbilical cord or may be derived from bone marrow, adipose tissue or blood.

In specific embodiments, the stem cells are bone marrow-derived human mesenchymal stem cells or adipose tissue-derived human mesenchymal stem cells.

In certain embodiments, the stem cells are mammalian, preferably human. In more specific embodiments, the human stem cells are allogeneic or autologous, preferably autologous.

In certain embodiments, the mammal is a human or a domesticated animal such as dog, horse and cat. In particular, the mammal is a human.

In certain embodiments, the damaged tissue that may be repaired by the method of the present invention is selected from cartilage or bone tissue. Therefore, the multi-compartment hydrogel of the present invention may be particularly useful in the repair or regeneration of articular injuries such as hyaline cartilage injury, chondrolysis, subchondral bone defects, joint incongruity, and post-traumatic arthritis. Articular injuries with subchondral defects include but are not limited to tibial plateau injury, pilon injuries, distal radius fracture and calcaneal fracture. Damaged organs such as articulated joints, for example, but not limited to, the knee, elbow and ankle, are particular amenable to repair according to the present invention. Accordingly, the multi-compartment hydrogel of the present invention may be particularly useful in the treatment of sport-related injuries to the joints or articular damage caused by a disease such as osteoarthritis, osteochondritis and osteonecrosis.

Since TGF-β1 and BMP-4 induce differentiation of stem cells into chondrocytes and osteoclasts, respectively, in certain embodiments, the multi-compartment hydrogel has two compartments, wherein the first compartment comprises a bioconjugate of alginate sulfate and TGFβ1, and the second compartment comprises a bioconjugate of alginate sulfate and BMP-4.

In a particular such embodiment, the cells migrating from tissue surrounding a wound into said first compartment interact with TGFβ1 and therefore differentiate into articular cartilage, and cells migrating from the tissue into the second compartment interact with MBP-4 and therefore differentiate into woven bone.

In certain embodiments, the multi-compartment hydrogel comprising TGF-β1 and BMP-4 is for use in regeneration of articular cartilage and/or woven bone or for use in repair of a subchondral defect.

In certain embodiments, the sulfated polysaccharide and the bioactive polypeptides of the kit defined herein above are each contained separately, each in a separate container.

In other certain embodiments, the sulfated polysaccharide is contained with at least one of the bioactive polypeptides.

In other certain embodiments, at least two of the bioactive polypeptides are contained together, in the same container.

In certain embodiments, the kit is intended for forming the multi-compartment hydrogel in a void in a damaged tissue in a mammal.

In other embodiments, the multi-compartment hydrogel is constructed, using the components of the kit, in a void in a damaged tissue in a mammal.

The invention will now be described with reference to some non-limiting examples.

EXAMPLES

Materials and Animals

Sodium alginates (VLVG, LVG, >65% guluronic acid monomer content) were from FMC Biopolymers (Drammen, Norway). Alginate-sulfate was synthesized from sodium alginate (VLVG) as previously described (Freeman I. et al., 2008). Human recombinant transforming growth factor β1 (TGF-β1) and human bone morphogenetic protein-4 (BMP-4) were from Peprotech (Rocky Hill, N.J.). High-glucose Dulbecco's modified Eagle's medium (DMEM), fetal bovine serum (FBS), L-glutamine, penicillin streptomycin and neomycin (Pen-Strep Neomycin), ITS+ Premix and Phosphate Buffer Saline (PBS) were all from Biological Industries (Kibbutz Beit Haemek, Israel). BMP-4 Enzyme-Linked Immuno-sorbent Assay (ELISA) kit and Sircol Collagen Assay kit were from R&D Systems (Minneapolis, Minn.). Anti-total ERK1/2 and dual-phosphorylated (threonine/tyrosine) ERK1/2 were from Cell Signaling (Danvers, Mass.) and Sigma-Aldrich (Rehovot, Israel). Rabbit polyclonal anti-collagen Type-II was from Novus Biologicals (Littleton, Colo.) and anti-human aggrecan G1-IGD-G2 domains from R&D Systems. Anti-rabbit HRP-conjugated secondary antibody was from Pierce Biotechnology (Rockford, Ill.), and anti-mouse HRP-conjugated secondary antibody was from Sigma-Aldrich. All other chemicals, unless specified otherwise, were from Sigma Aldrich, and were analytical-grade.

Adult New Zealand White Rabbits (female, 8 months, 4.5 kg) were acquired from Charles River (Germany). Routine blood examination was performed prior to operation and before euthanasia. Adult Sinclair mini-pigs (male, 13 months, 40 kg) were acquired from Harlan laboratories (Jerusalem, Israel). The experiments were conducted under an ethic committee approved protocol in accordance with local legislation and guidelines. Routine blood examination was performed prior to operation, and at 3 months after operation.

Methods

Surface Plasmon Resonance.

Surface Plasmon Resonance (SPR) analysis for BMP-4 binding onto immobilized alginate-sulfate was carried out as previously described (Freeman I. et al., 2008, Freeman I. et al., 2009) using the BIAcore 3000 instrument (Pharmacia, Uppsala, Sweden). Biotinylated samples of heparin, as a positive control, alginate-sulfate and alginate were immobilized onto the channels on a streptavidin (SA)-modified sensor chip. Binding measurements were performed over a range of concentrations of the protein, between 60-180 nM. Association and dissociation rate constants were calculated by nonlinear curve fitting of the primary sensorgrams using the Langmuir binding model available in the BIA evaluation 3.2 Software. The affinity binding constants ($K_A$) were calculated from the association and dissociation rate constants, using the same software.

Statistical Analysis.

Statistical analysis was performed with GraphPad Prism version 5.03 for Windows (GraphPad Software, San Diego, Calif.). All variables are expressed as mean±SEM. Quantifications of loaded BMP-4 and collagen deposition were compared by two-tailed unpaired t test. Statistical analysis of the data on ALP activity was performed by 2-way analysis of variance (ANOVA); Bonferroni's post-hoc test was carried out to determine differences between the treatments. Statistical analysis of the data on ERK1/2 phosphorylation was performed by 1-way ANOVA at each time point, Dunnet's post-hoc test was carried out to determine differences between the treatments. $P<0.05$ was considered statistically significant.

Macroporous Scaffold for In Vitro Studies.

TGF-β1 or BMP-4 (50 µg/mL) in citric acid (10 mM, pH 3) was incubated with alginate-sulfate solution (2.5% w/v) for 1.5 h at 37° C., to allow equilibrium binding of the factor. The bioconjugate solution was mixed with a solution of calcium cross-linked alginate, prepared by mixing the alginate solution with D-gluconic acid/hemicalcium salt solution using homogenization to distribute the calcium ions throughout the solution (Ruvinov E. et al., 2010, Ruvinov E. et al., 2011). The final mixture consisted of 0.1% alginate-sulfate (w/v), 1% alginate (w/v) and 0.18% (w/v) D-gluconic acid/hemicalcium salt.

Macroporous scaffolds were fabricated from the above mixture by a freeze-dry technique to yield a ~90% porous sponge, with interconnected pores in the size range of 65-85 µm (Shapiro L. et al., 1997). The scaffolds were sterilized by exposure to UV light for 30 min in a biological cabinet, prior to cell seeding. In control scaffolds, the factor was directly mixed with calcium cross-linked alginate solution and fabricated into macroporous scaffolds in the same manner. The amount of loaded TGF-β1 or BMP-4 per scaffold was 200 ng.

For construction of the bi-layered in vitro system, half of the scaffolds containing either TGF-β1 (100 ng) or BMP-4 (100 ng) were initially prepared as described above (FIG. 1, above the dashed line). After cell seeding and a short culture of 2 days (as described below) the seeded scaffolds were combined together by their assembly on a stainless steel pin, perpendicular to a supporting polydimethylsiloxane (PDMS) layer (FIG. 1, below the dashed line).

Hydrogel for In Vivo Studies.

For the in vivo studies, the bilayer hydrogels were formed in-situ in the subchondral defect by injecting, layer-by-layer, first the BMP-4/affinity-bound alginate solution followed by the TGF-β1/affinity-bound alginate solution (FIG. 2). The alginate solutions were essentially prepared as described above, by first binding of the individual factor to alginate-sulfate followed by mixing with partially calcium cross-linked alginate solution. Here the amount of loaded factor in each layer was 300 ng.

Evaluation of BMP-4 Protein Bioactivity.

BMP-4 bioactivity in the scaffold was evaluated by quantification of collagen deposition in a monolayer of rat cardio-fibroblasts, seeded in 24-well plates (150,000 cells/well). BMP-4 affinity-bound scaffolds were incubated for 24 h at 37° C., after which the medium containing released BMP-4 was collected and added to the monolayer cultures. Collagen deposition was determined after three days, using the Sircol colorimetric assay, as previously described (Re'em T. et al., 2012, Kohan M. et al., 2009).

Isolation of MSCs from Human Bone Marrow.

Human MSCs were generated from bone marrow aspirates of healthy donors, collected after informed consent, as described in (Re'em T. et al., 2012). The isolated cell fraction was suspended in culture medium (high-glucose DMEM, supplemented with 10% (v/v) FBS, 100 U/mL penicillin, and 0.1 mg/mL streptomycin, 0.1 mg/mL neomycin and 1% L-Glutamine) and plated on tissue culture plates for 24 h, followed by removal of non-adherent cells. The adherent cells were expanded until reaching 50% confluence, at which time they were removed from the plate by trypsin and re-plated at a density of $1\times10^3$ cells/cm$^2$. Cell stemness was confirmed by following their differentiation, spontaneously and upon induction, into osteoblasts, adipocytes and chondroblasts, assessed using von Kossa, Oil-red-O and Safranin-O staining, respectively (Levy O. et al., 2008). In all experiments, pre-confluent, twice-expanded cells (i.e. 3 passages) were used.

Cell Seeding and Cultivation in Scaffolds.

Cell seeding onto the scaffold was attained by dropping 15 μL of the cell suspension onto a dry scaffold ($2$-$3\times10^5$ cells/scaffold), followed by 2-min centrifugation (107 g, 4° C.) and a short (30 min) incubation (37° C., 5% $CO_2$) in 50 μL culture medium. The cell constructs were then transferred to 12-well plates, and basal chemically-defined serum-free medium was added (2 mL/well). The medium consisted of high-glucose DMEM, supplemented with 50 μg/mL ascorbate-2-phosphate, 100 μg/mL sodium pyruvate, 40 μg/mL proline, 100 U/mL penicillin, 0.1 mg/mL streptomycin, 0.1 mg/mL Neomycin, 1% ITS+Premix (6.25 μg/mL insulin, 6.25 μg/mL transferrin, 6.25 μg/mL, 6.25 ng/mL selenious acid, 1.25 mg/mL BSA, 5.35 mg/mL linoleic acid), 100 nM dexamethasone and 5 mM beta-glycerophosphate. The cell constructs were cultivated at 37° C., in a 5% $CO_2$ humidified incubator. Half of the medium was replaced once a week.

The DNA content in cell constructs was measured after dissolving the scaffolds in citrate buffer (6% w/v in PBS, pH 7.4) to free the cells. Cell pellets were further dissolved in 0.5 mL papain solution (5 mM EDTA, L-cysteine, 155 mM NaCl, pH 6.8) and incubated at 65° C. overnight. The supernatant was stored at −80° C. until analysis for DNA content using bisbenzimidazole Hoechst 33258 dye.

Western Blotting.

Cell constructs were dissolved with citrate buffer (6% w/v in PBS, pH 7.4) to free the cells. The mixture was centrifuged and the cell pellets were frozen in liquid nitrogen and stored at −80° C. until analysis. The cell pellets were suspended in lysis buffer (10% glycerol, 25 mM NaCl, 50 mM NaF, 10 mM pyrophosphate, 2 mM EGTA, 2 mM DTT, 20 mM P-Nitro-phenyl-pi, 25 mM Trizma, 2 mM $Na_2VO_4$, 100 μM MSF, 10 μg/ml leupeptin, 5.74 μg/ml aprotinin and 0.1% (v/v) Triton X-100), centrifuged and the total extracted protein was measured using Bradford reagent assay (Bio-Rad), using BSA as standard. Cell extracts were separated by 10% (w/v) sodium dodecyl sulfate polyacrylamide gel electrophoresis (SDS-PAGE) then transferred to nitrocellulose membranes (Schleicher & Schuell, Keene, NL) and blocked in 5% (w/v) non-fat milk solution. The membranes were incubated with mouse anti-phospho-ERK1/2 and rabbit anti-total ERK1/2 antibodies followed by incubation with anti-mouse and anti-rabbit HRP-conjugated secondary antibodies, respectively. The membranes were developed using standard enhanced chemiluminescence (ECL) procedure (Amersham, GE Healthcare, Buckinghamshire, UK). The signal was detected by Biomax film (Kodak, Rochester, N.Y.). Densitometry analysis was carried out using ImageJ software (National Institutes of Health; http://rsbweb.nih.gov/ij/). The levels of phosphorylation were quantified by the measuring the band intensity of phospho-ERK1/2 relative to the total intensity of ERK1/2. The relative intensity was normalized to the expression level measured in control 1-day cultures of affinity-binding scaffolds w/o BMP-4 supplementation.

Alkaline Phosphatase Activity.

Alkaline phosphatase (ALP) activity was measured using the ALP assay kit (MD Biosciences, Minn.). Briefly, freed cells from the construct were washed with PBS, lysed for 20 min in 0.2% (v/v) NP-40, then transferred into a 96-well plate and incubated with the working solution, according to the manufacturer's instructions. Essentially, this kit relies on the hydrolysis of p-nitrophenyl phosphate by ALP, forming yellow colored p-nitrophenol (maximal absorbance 405 nm). ALP activity was normalized to DNA content.

Histology and Immunostaining, In Vitro Studies.

Cell constructs were gradually dehydrated by soaking in alcohol solutions (70-100%), paraffin-embedded, cut into 5-μm-thick sections, mounted on slides and stained with hematoxylin & eosin (H&E) for detecting nucleus and cytoplasm, respectively, or immunostained with anti-collagen type II antibody, anti-human aggrecan G1-IGD-G2 domains. In the case of the latter, cross-sections were co-stained with hematoxylin. To detect phosphate salt deposits, typical during osteogenic differentiation, cross-sections of hMSC constructs were stained using von Kossa reagent (Bills C E. et al., 1971) and Nuclear Fast Red solution for counter-staining.

Subchondral Defect Model in New Zealand White Rabbits.

All rabbits were premedicated with intramuscular injections of 25 mg kg$^{-1}$ ketamine hydrochloride and 1 mg kg$^{-1}$ midazolam. As an analgetic the rabbits received subcutaneous injections of 0.03 mg kg$^{-1}$ buprenorphine. General anaesthesia was induced by 1 mg kg$^{-1}$ propofol intravenously administrated. After endotracheal intubation the general anaesthesia was continued using isoflurane gas (2.5-3.5%/oxygen mixture, 1.5-2.0 l min$^{-1}$) with spontaneous respiration. Infusions of Ringer's lactate solution (10 mL kg$^{-1}$ h$^{-1}$) ensured cardiovascular function. Both legs were clipped and aseptically prepared for surgery. An anteromedial approach to the medial femur condyle was used in the surgical procedure. The surgery procedure in adult New Zealand White rabbit is depicted in FIG. 2A-2D. Subchondral defects (in each leg) were created in the patello-femoral groove by a hand-operated drill (diameter 3 mm, depth 3 mm) to prevent drill-related heat necrosis at the implant site. The drilled subchondral defect was first filled with 10 µL of BMP-4/affinity-binding alginate solution and gelation was induced by adding 10 µL of 1 M $CaCl_2$. After an instant gelation of the bottom layer, the top layer of TGF-β1/affinity-binding alginate was similarly constructed. Each alginate layer was loaded with 300-400 ng of BMP-4 or TGF-β1. In control rabbits, the drill-hole was left untreated. The rabbits were allowed to move freely in their cages with full load-bearing and no external support. The rabbits were killed 2 and 4 weeks post-operation and treatment.

Micro Computer-Tomography (µCT).

The explants were frozen and scanned by µCT (v|tome|x L 240, GE, Phoenix, Wunstorf, Germany) to follow bone formation in the drill-hole. The maximum energy of the polychromatic photon spectrum emitted by the microfocus X-ray tube was limited to 180 keV and an electron current of 90 µA was set. The radioscopic images were acquired in cone-beam geometry with a circular orbit of the radiation source. Tomograms, consisting of 500×500×500 voxels, were reconstructed utilizing the Feldkamp algorithm. Each of the cubical voxels had an edge length of about 24 µm.

Histology and Toluidine Blue Staining.

Explants were fixed in 4% para-formaldehyde (v/v, in PBS, pH 7.4) for 7 d. After embedding and polymerization in methyl-methacrylate (Technovit 9100 Newl, Heraeus-Kulzer, Hanau, Germany), thin sections (5 µm thick) were cut using RM 2155 microtome (Leica, Bensheim, Germany). Prior to performing staining, sections were deacrylated in xylol (2×15 min) and 2-methoxyethylacetate (2×10 min), cleared in a decreasing ethanol series (2×isopropyl alcohol, 2×96% ethanol, 2×70% ethanol, 2 min each), and rehydrated in distilled water. Rehydrated sections were incubated in 0.1% Toluidine blue O (Sigma) for 20 s, washed in distilled water, dehydrated in ethanol, and mounted in Eukitt (Labonord, Monchengladbach, Germany).

The binding and activity of attached factors in the affinity binding system, as well as their differentiation induction capabilities, were initially evaluated in separate experiments to eliminate interactions or interference between the factors. Following this, the spatial differentiation of hMSCs in the TGF-β1/BMP-4 bi-layer scaffold was examined to validate regeneration of the osteochondral interface.

The results of the affinity binding of TGF-β1 to alginate-sulfate/alginate scaffold were recently published (Re'em T. et al., 2012), demonstrating that such binding maintained the factor's activity, enabled its sustained release and promoted hMSC differentiation towards committed chondrocytes.

Example 1

BMP-4 Binding and Activity

To validate BMP-4 binding to alginate-sulfate, SPR analysis was performed, revealing a strong and specific binding of BMP-4 to alginate-sulfate ($K_A=5.63\times10^9$ $M^{-1}$). The affinity binding of BMP-4 to alginate-sulfate/alginate scaffold enabled its protection during fabrication; the total amount of loaded BMP-4, determined by ELISA, was 1.5-times greater in the affinity-bound scaffolds than in scaffolds with no alginate-sulfate (59.37±1.34 ng vs. 39.49±2.6 ng in the control, (p<0.05)).

Figure 3:
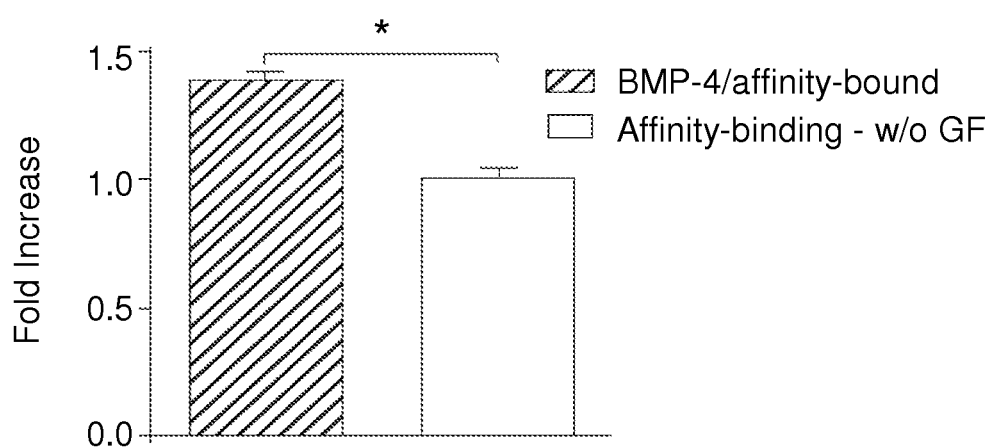
FIG. 3 shows bioactivity of released BMP-4 protein. The bioactivity of released BMP-4 from BMP-4/affinity-bound scaffolds was evaluated by its ability to enhance collagen deposition in rat cardio-fibroblast monolayer cultures. The degree of collagen deposition was determined after three days, using the Sircol colorimetric assay. Values are normalized to the degree of collagen deposition in fibroblasts cultured with released medium from empty scaffolds. *p=0.0004 (two-tailed unpaired t test).

To ensure BMP-4 bioactivity, monolayers of rat cardio-fibroblasts were treated with the released medium from BMP-4/affinity binding scaffolds. The released medium, collected at day 1 of the release study, was diluted to a BMP-4 concentration of 9 ng/mL, and BMP-4 bioactivity was assessed by its ability to enhance collagen production in these cultures (FIG. 3). Collagen deposition was significantly greater in the cultures exposed for 3 days to medium collected from BMP-4/affinity binding scaffold compared to the control medium, released from empty scaffolds (p=0.0004).

Example 2

BMP-4-Induced MAPK Signaling Pathway in hMSC Cultures

Figure 4A:
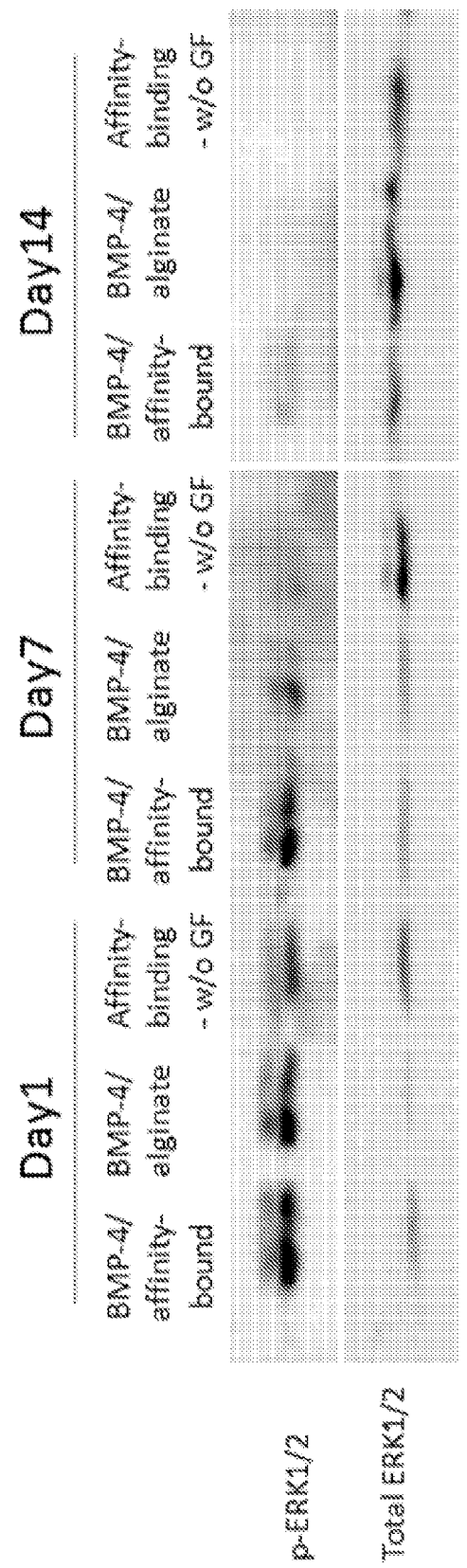
FIGS. 4A-B depict assays showing prolonged BMP-4-induced activation of MAPK signaling pathway in human mesenchymal stem cells (hMSCs) cultured within affinity-binding scaffolds. The BMP-4/MAPK signaling pathway was examined by Western blotting, 1, 7 and 14 days post-seeding. Results represent a pool of cells extracted from 5-7 constructs per time point. (A) Representative ERK1/2 Western blots. (B) Densitometric analysis of ERK1/2 Western blots. Levels of phosphorylation were quantified by the band intensity of phospho-ERK1/2 (p ER K) relative to total ERK1/2. The relative intensity was normalized to the expression level in control of affinity-binding scaffolds without (w/o) BMP-4, on day 1. p=0.097, 0.008, 0.029, on day 1, 7 and 14, respectively (one-way ANOVA). *p<0.05 (Dunnet's post-test), when compared to BMP-4/affinity-bound.
Figure 4B:
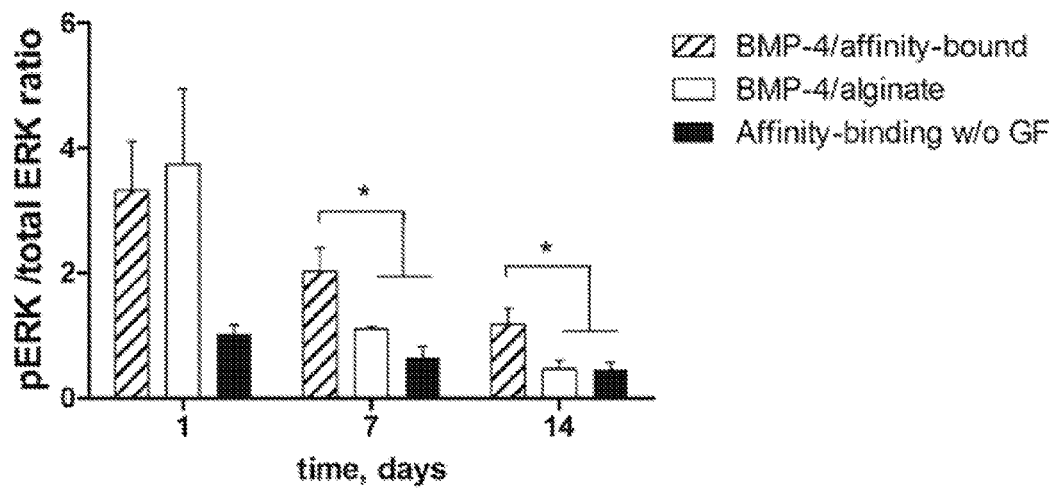

BMP-4 activation of MAPK signal-transduction pathway, known to be involved in hMSC osteogenic differentiation (Levy O. et al., 2010, Kozawa O. et al., 2002) was evaluated by Western blot analysis in hMSC constructs (FIG. 4A). The ERK1/2 phosphorylation levels were significantly greater (p<0.05) in the BMP-4/affinity-bound constructs than in control constructs on days 7 and 14, indicating the long-term bioactivity of the locally presented BMP-4 in these scaffolds (FIG. 4B). In cell constructs with no BMP-4 supplementation, the activation of ERK1/2 was significantly lower (p<0.05).

Example 3

BMP-4-Induced Osteogenic Differentiation in hMSC Construct

Figure 5A:
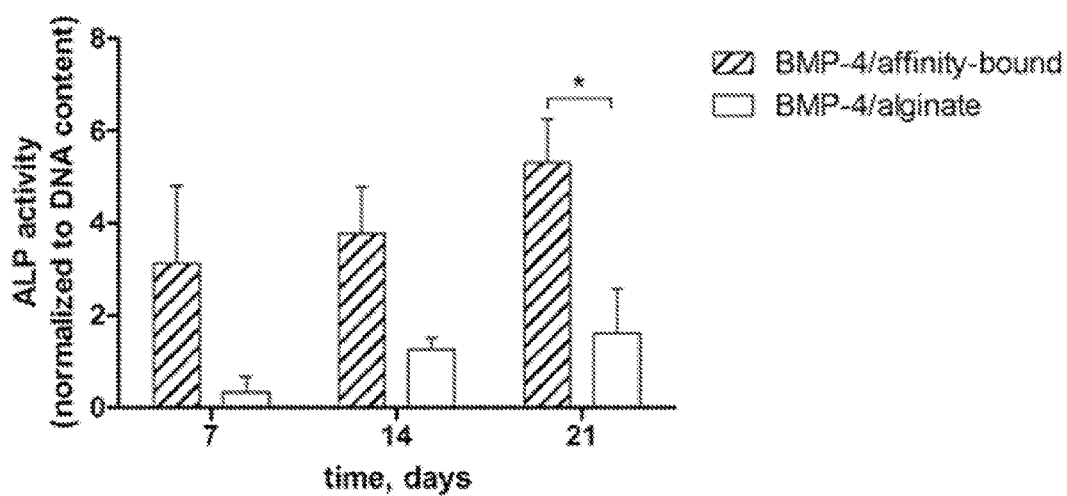
FIGS. 5A-B show BMP-4-induced osteogenic differentiation in hMSC constructs. (A) Alkaline phosphatase (ALP) activity levels in hMSC constructs, cultivated in BMP-4/affinity-bound scaffold and BMP-4/alginate scaffolds, *p<0.05 (Bonferroni post-test, 2-way ANOVA). (B) Von Kossa staining for mineralized bone matrix in thin sections (5 μm) in 3 week-old hMSC constructs (Bar: 50 μm). Left panel—BMP-4/affinity-bound scaffold; Right panel—BMP-4/alginate scaffold.
Figure 5B:
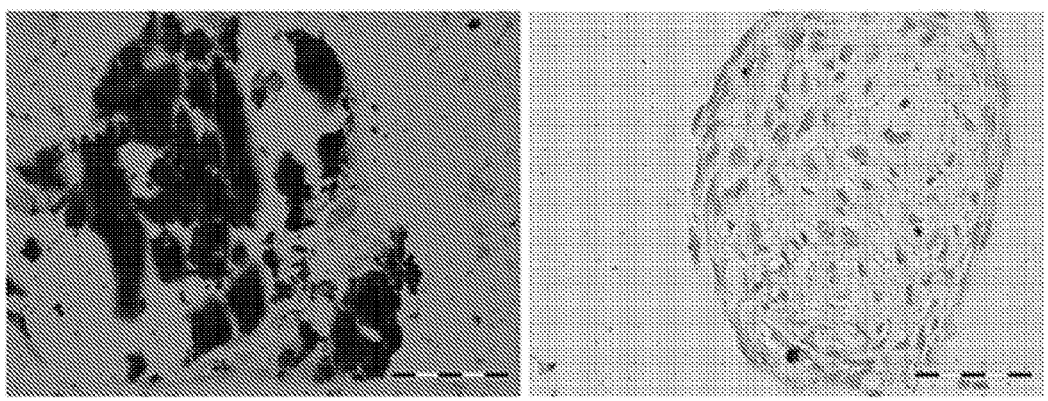

The osteogenic differentiation of hMSCs within BMP-4/affinity-bound scaffold was evaluated by measuring the alkaline phosphatase (ALP) activity, a known marker for osteogenic differentiation (Qi H. et al., 2003) (FIG. 5A), and by following the deposition of mineralized bone matrix (FIG. 5B). Significantly greater ALP activity levels were detected after 3 weeks of cultivation in BMP-4/affinity-bound scaffolds, compared to the levels in BMP-4/adsorbed (alginate) scaffolds (p<0.05). Additionally, von Kossa staining indicated the presence of massive mineralized bone matrix deposition in the BMP-4/affinity-bound scaffold, after 3 weeks (FIG. 5B). Of note, the DNA content, determined by Hoechst assay, was similar in all constructs (data not shown), indicating that the greater deposition of mineralized bone matrix in the affinity-binding constructs is due to the sustained presentation of BMP-4 and its prolonged activity as an osteogenic inducer in this culture.

Example 4

Osteochondral Differentiation in the Bilayered System, In Vitro

Figure 6B:
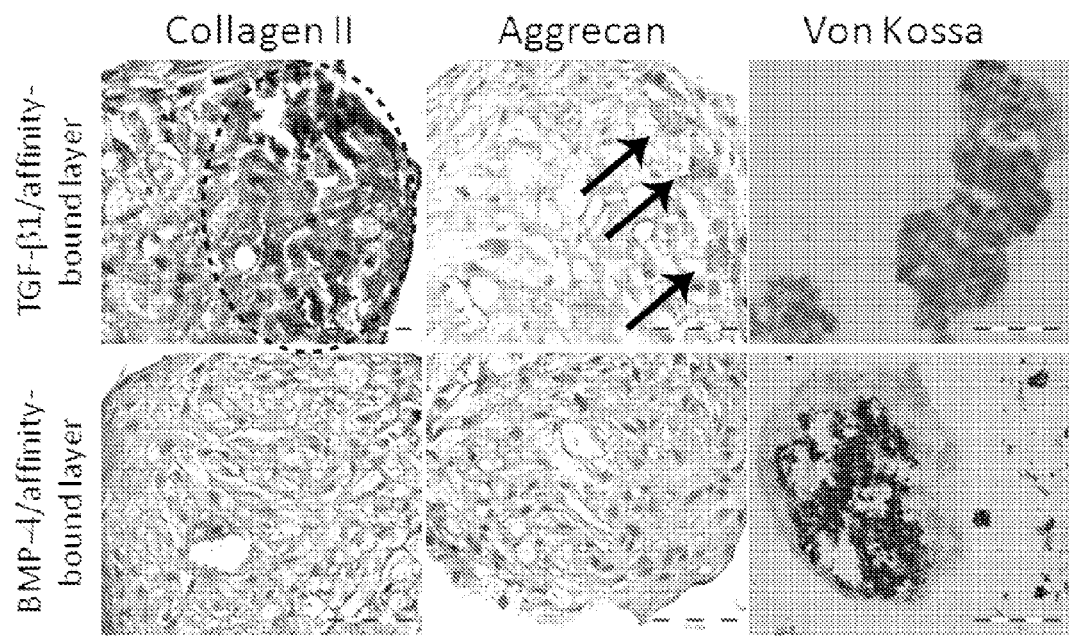

The capability of the bilayer system to induce a spatial differentiation pattern of hMSCs, either to chondrocytes or osteoblasts, according to the respective affinity-bound factor in the layer, was evaluated by measuring the ALP activity in each layer, as well as by immuno-staining for the presence of aggrecan, collagen type II and staining for von Kossa (FIG. 6B).

The ALP activity was significantly greater in the BMP-4 layer, either as part of the bi-layer system or as a stand-alone layer, compared to the activity seen in the TGF-β1-bound layer(s) (FIG. 6A, p<0.05). Type-II collagen and aggrecan, major cartilage ECM components, were more prominently present in the TGF-β1/affinity bound layer, compared to the BMP-4/affinity-bound layer. Von Kossa staining confirmed that the mineralization process was limited to the BMP-4 layer (FIG. 6B).

Example 5

Subchondral Defect Model in Rabbits

Figure 2A:
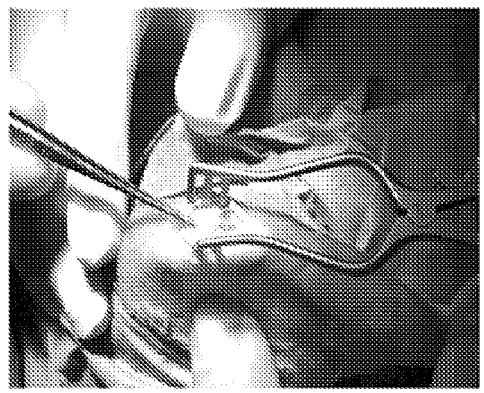
FIGS. 2A-E depict the surgery procedure for creating the osteochondral defect and in situ construction of the bi-layer hydrogel, spatially presenting TGF-β1 at top layer and BMP-4 at bottom layer. (A-C) A subchondral defect was created in the patello-femoral bone by a hand-operated drill to create a hole (3 mm diameter, 3 mm deep) in the patella groove. (D) The irregular subchondral defect was filled with in situ formed hydrogel, constructed layer-by-layer; (E) first, the BMP-4/affinity-bound alginate solution was administrated to the hole and after gelation, the top layer of TGF-β1/affinity-bound alginate solution was added to fill up the defect until the original chondral joint surface.
Figure 2B:
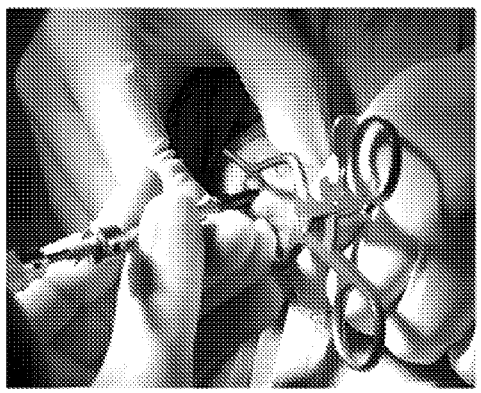
Figure 2C:
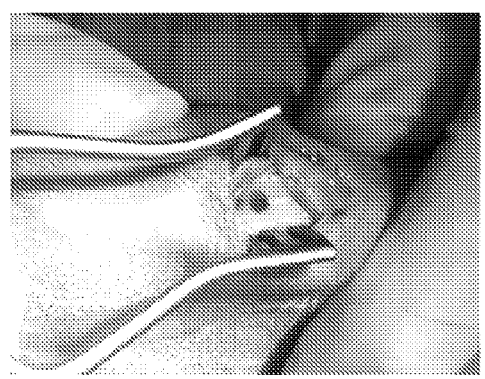
Figure 2D:
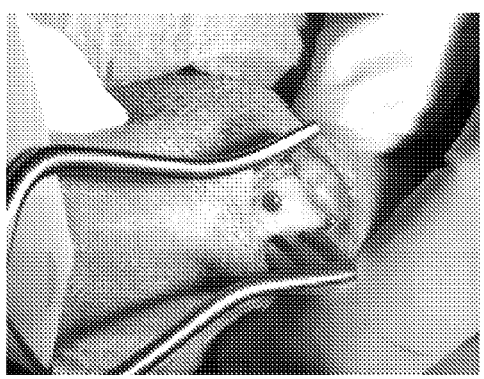
Figure 2E:
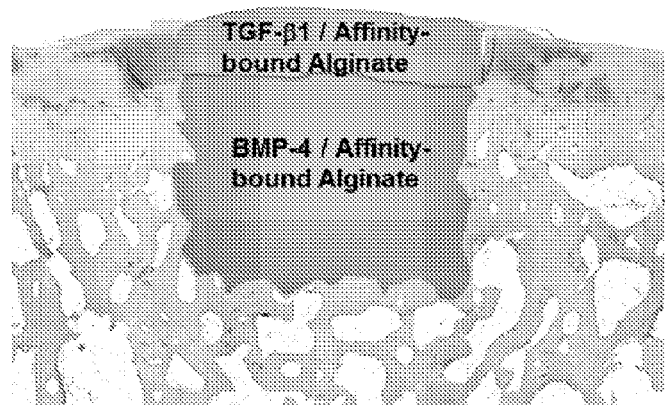

After proving the capability of the bilayer system to induce spatial differentiation of seeded hMSCs in vitro, the inventors sought to test its capability to do so for migrating cells, in a subchondral defect in rabbits. The acellular in-situ formed hydrogel was constructed layer-by-layer; the BMP-4/affinity-bound alginate layer was first constructed in the hole, followed by layering the TGF-β1/affinity-bound alginate on top (FIG. 2E).

Figure 7:
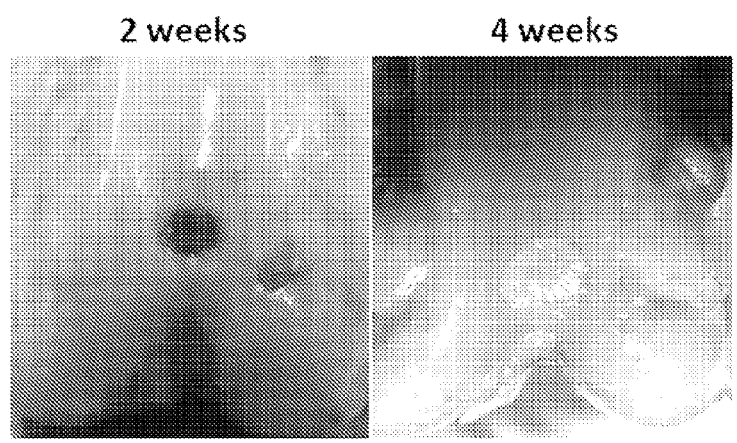
FIG. 7 illustrates gross morphology of the explants in subchondral defect. The acellular bi-layer system with affinity-bound TGF-β1 in the top layer and BMP-4 in the bottom layer was constructed in situ, layer-by-layer, in a subchondral defect in rabbits. Pictures reveal the gross morphology of the defect, two- (left panel) and four- (right panel) weeks after implantation.

Gross morphology of the explants, 2 weeks post-operation, demonstrated the integration of hydrogel with the surrounding tissues. Four weeks post-operation, a newly-formed white tissue, typical of a cartilaginous tissue, was seen to cover the defect and was well-integrated with the surrounding articular cartilage (FIG. 7).

Example 6

Histology for Evaluation of Cartilage Formation

Figure 8A:
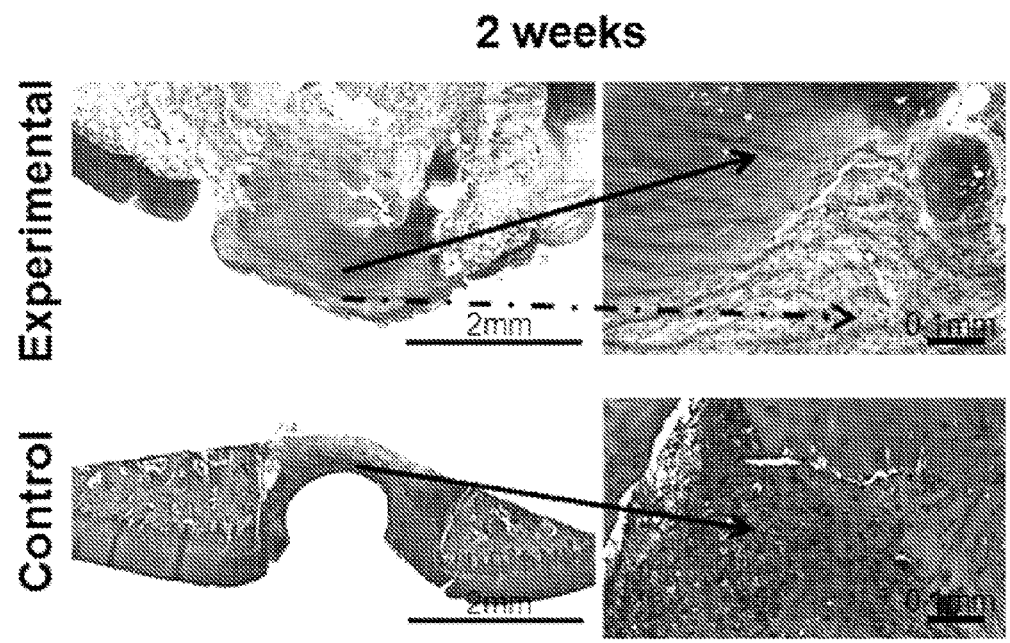
FIGS. 8A-B illustrate toluidine blue staining for evaluation of cartilage formation in a subchondral defect. Toluidine blue staining of thin sections (5 μm) from two- (A) and four (B) -week explants for cartilage proteoglycan detection. Arrows denote the area of magnification (Bar: A, upper and lower left; B, upper and lower left—2 mm. Bar: A, upper and lower right; B, upper and lower right—0.1 mm).
Figure 8B:
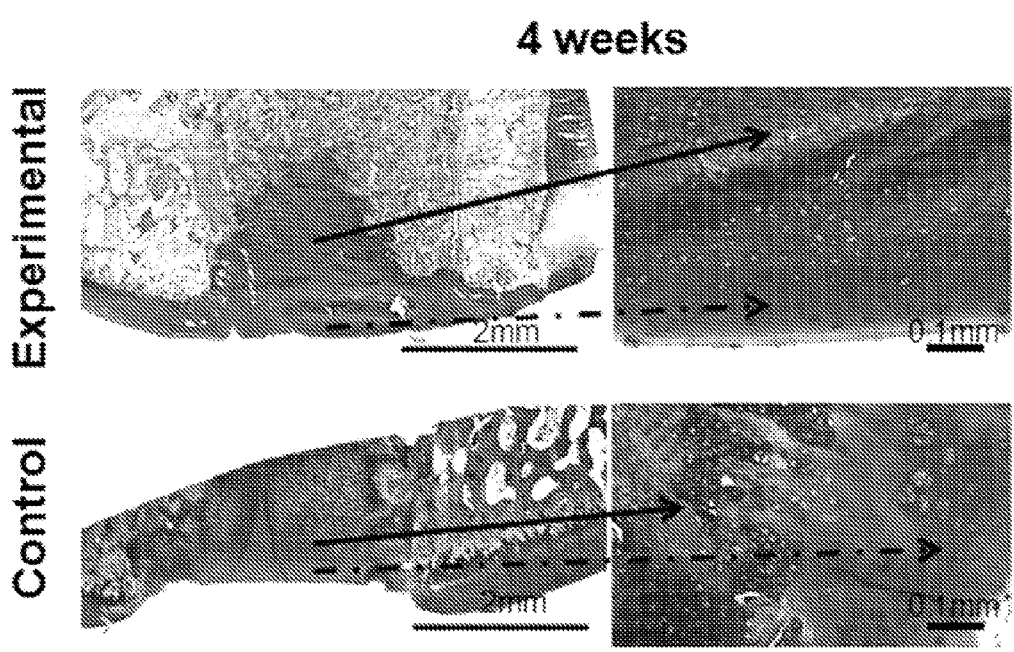

Toluidine blue staining of 2-week explants, for cartilage proteoglycan detection, indicated the formation of a new cartilage layer at the top, clearly distinguishable from the bottom bone tissue (FIG. 8A). In 4-week explants, the deep purple color indicated the presence of richer cartilaginous ECM in the newly-formed cartilage layer as well as in the surrounding cartilage tissue. The newly-formed cartilage was shown to be well integrated with the surrounding cartilage tissue, and was clearly distinguishable from the bone phase found deeper in the drill hole (FIG. 8B). In control untreated animals, two weeks post-operation, the hole remained as is and no new cartilage or bone was detected. After 4 weeks, there was some filling of the drill hole, however, no two distinguishable cartilage and bone layers were detected.

Example 7

Immunostaining for Collagen Type II—a Specific Marker of Cartilage ECM

Figure 9A:
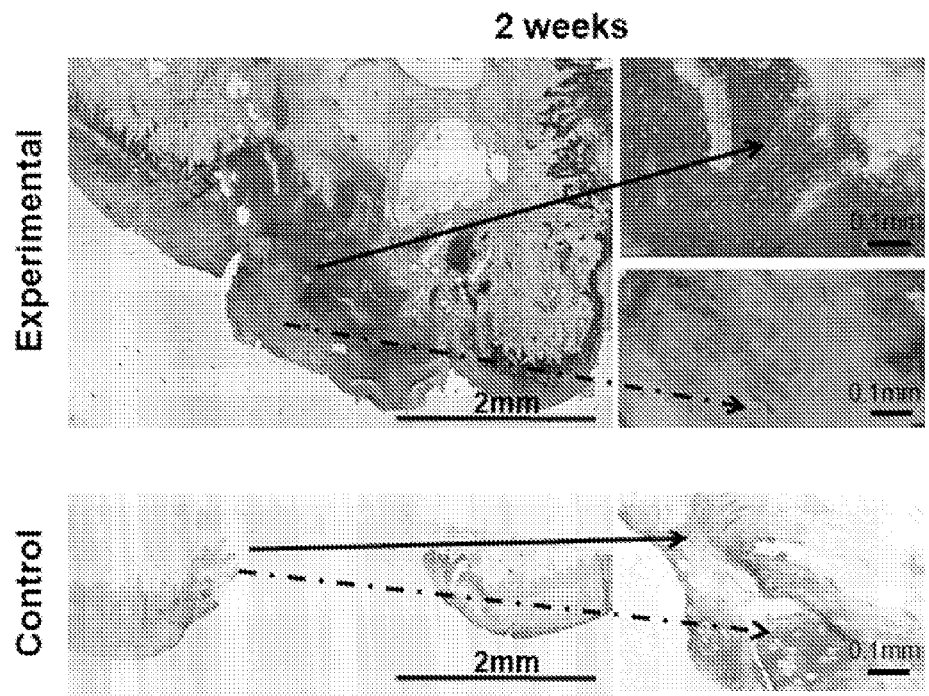
FIG. 9A-B illustrate immune-staining for collagen type II. Thin sections (5 μm) from the two- (A) and four (B) -week explants were immunostained for collagen type II, a marker for hyaline cartilage. Arrows denote the area of magnification (Bar: A, upper and lower left; B, upper and lower left—2 mm. Bar: A, upper, middle and lower right; B upper, middle and lower right—0.1 mm).
Figure 9B:
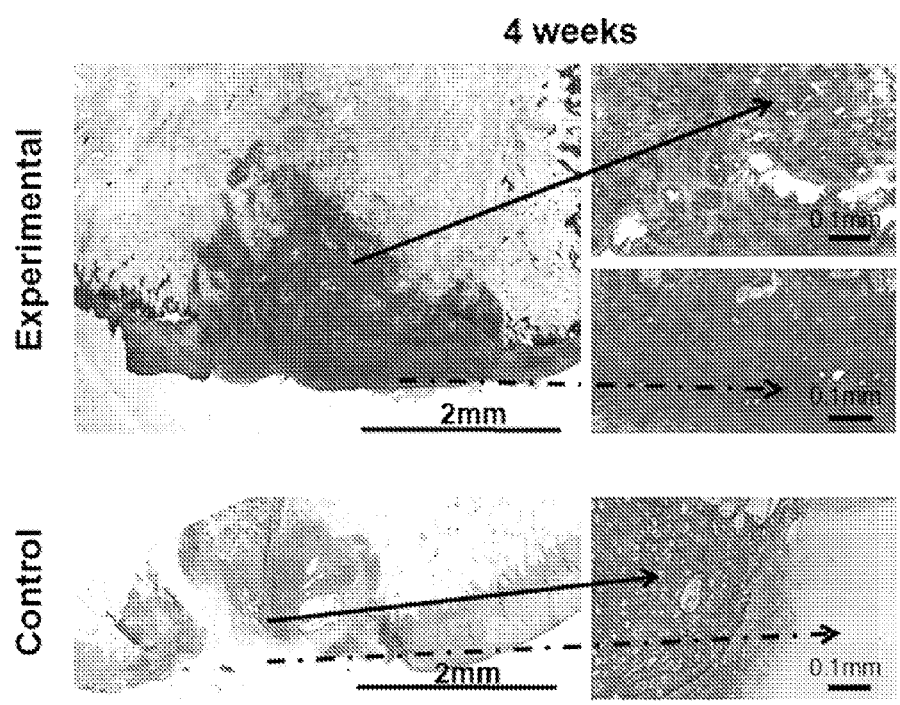

Immunostaining of the two-week explants for collagen type II, a major component in cartilaginous ECM, revealed the presence of two phases in the cartilage layer, well integrated to each other, but distinguishable from each other by the extent of staining to collagen type II and by cellularity (FIG. 9A, upper left panel). Higher magnification of the deeper phase (FIG. 9A, upper right panel, solid arrow) revealed the presence of mainly round cell morphology, typical for mature chondrocytes and strong staining for collagen type II. In the surface phase (FIG. 9A, middle right panel, dashed arrow) staining to collagen type II was weaker with fewer small size cells. In the four-week explants, the newly formed cartilage was well integrated with the surrounding native tissues, and was strongly stained for collagen type II, both in the depth and surface of the cartilage layer (FIG. 9B, upper left panel). A high-magnification image (FIG. 9B, upper right panel, solid arrow) revealed that the cells residing within the deeper layer of the cartilage had a round morphology and were relatively large (~20 µm diameter), indicative of slightly hypertrophic chondrocytes. At the surface of the cartilage layer (FIG. 9B, middle right panel, dashed arrow), the chondrocytes were evenly distributed and isolated from each other by the cartilaginous ECM, positively stained to collagen type II.

In control untreated animals, 2 weeks post-operation, the hole remained as it was, and no type II collagen was detected in the area of the drill hole (FIG. 9A, lower left panel). At high magnification (FIG. 9A, lower right panel), the surrounding cartilage in the rim of the drilled hole appeared to be transformed into hypertrophic cells. After 4 weeks, the filled tissue revealed a faint staining for collagen type II mainly in the deep layer (FIG. 9B, lower left panel). A high-magnification image indicated that the cells in the deep layer were mainly hypertrophic in nature (FIG. 9B, lower right panel).

Example 8

µCT for Evaluation of Bone Formation

Figure 10:
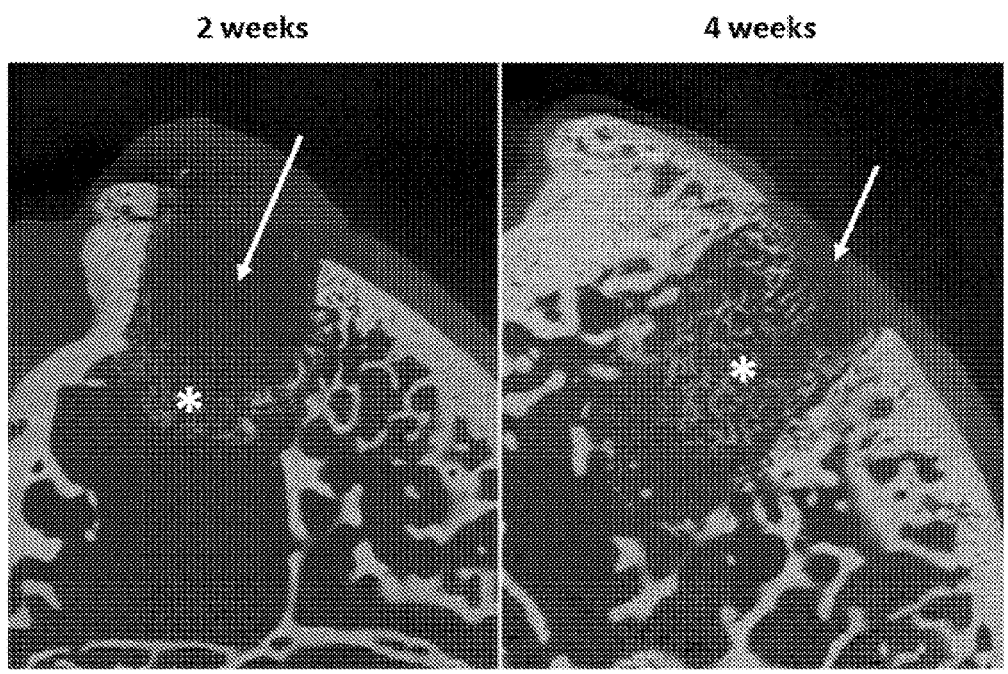
FIG. 10 shows microcomputer-tomography (μCT) for evaluation of bone formation. μCT scans of the explants revealing the formation of bone underneath the cartilage tissue. Asterisks denote woven bone formation, and arrows indicate the non-mineralized tissue.

Two weeks post-operation, microtomography scans revealed the presence of bone tissue at the bottom and rim of the drilled hole (FIG. 10). After 4 weeks, the formation of subchondral woven bone layer is clearly seen in the depth of the drilled hole (yellow arrow), where BMP-4 was present, while in the top soft tissue, where TGF-β1 was present, no mineralization process took place.

Example 9

Preclinical Study in Minipigs

Figure 11:
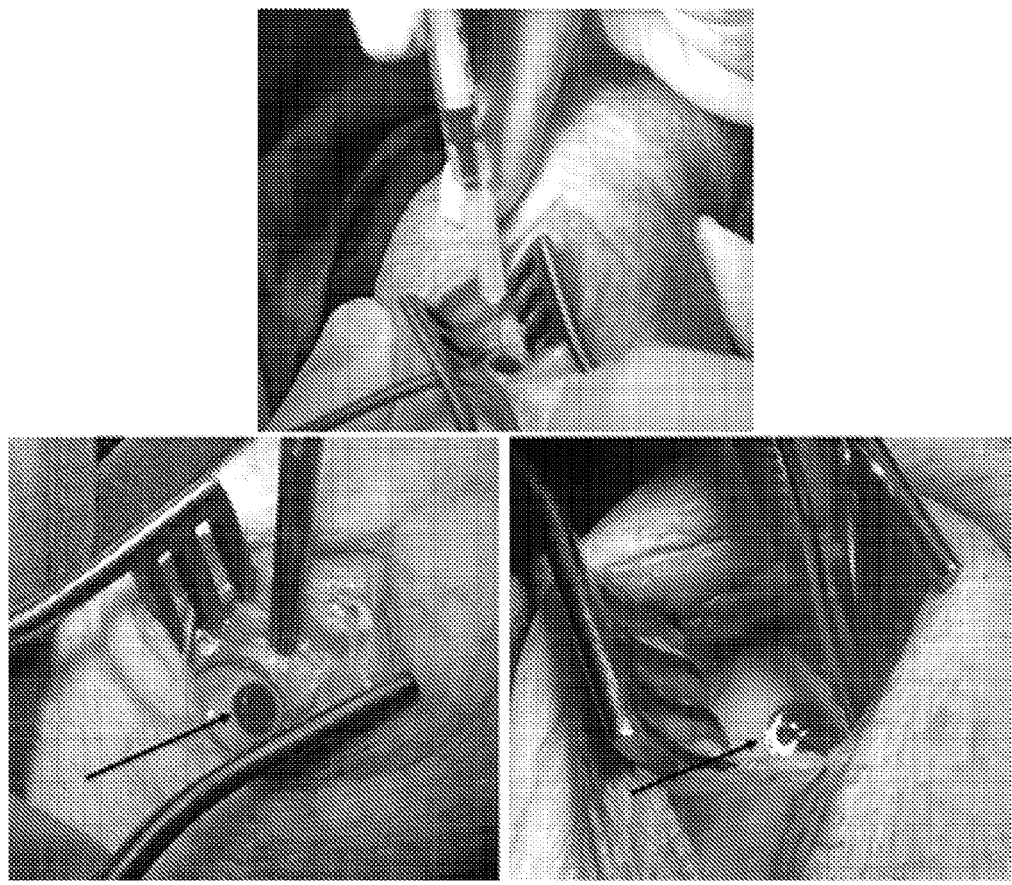
FIG. 11 illustrates a bilayer injectable system in a minipig. Biomaterial injection into the defect in minipig femoral condyle (upper panel). The appearance of the finally gelated material in the defect (lower panels). Note the smooth surface and complete filling at the defect edges.

The efficacy of bilayer system is being tested in preclinical study in minipigs, for the repair of osteochondral defects. The operation, filling, and gelation procedure revealed superior properties of the injected material. First, the injectable nature (FIG. 11, upper panel) of the material enables minimally invasive, arthroscopic administration in the future. Second, the resulting gelated material can be easily modified and reshaped intraoperatively by refilling and/or surface smoothing. Finally, the gelated material sticks well in the defect, has a smooth surface, and is not removed or deformed by knee bending (FIG. 11, lower panels). These material properties represent a significant advantage over other strategies, which utilize solid or liquid formulations.

REFERENCES

Bills C E, Eisenberg H, Pallante S L. Complexes of organic acids with calcium phosphate: the von Kossa stain as a clue to the composition of bone mineral. Johns Hopkins Med J 1971; 128:194-207.

Capila I., and Linhardt R. J. Heparin-Protein Interactions. Angewandte Chem Int. Ed., 2002; 41:390-412.

Crawford D C, Heveran C M, Cannon W D, Jr., Foo L F, Potter H G. An autologous cartilage tissue implant NeoCart for treatment of grade III chondral injury to the distal femur: prospective clinical safety trial at 2 years. Am J Sports Med 2009; 37:1334-43.

Dvir T, Kedem A, Ruvinov E, Levy O, Freeman I, Landa N, et al. Prevascularization of cardiac patch on the omentum improves its therapeutic outcome. Proc Natl Acad Sci USA 2009; 106:14990-5.

Freeman I, Kedem A, Cohen S. The effect of sulfation of alginate hydrogels on the specific binding and controlled release of heparin-binding proteins. Biomaterials 2008; 29:3260-8.

Freeman I, Cohen S. The influence of the sequential delivery of angiogenic factors from affinity-binding alginate scaffolds on vascularization. Biomaterials 2009; 30:2122-31.

Gotterbarm T, Richter W, Jung M, Berardi Vilei S, Mainil-Varlet P, Yamashita T, et al. An in vivo study of a growth-factor enhanced, cell free, two-layered collagen-tricalcium phosphate in deep osteochondral defects. Biomaterials 2006; 27:3387-95.

Karp J M, Leng Teo G S. Mesenchymal stem cell homing: the devil is in the details. Cell Stem Cell 2009; 4:206-16.

Kohan M, Breuer R, Berkman N. Osteopontin induces airway remodeling and lung fibroblast activation in a murine model of asthma. Am J Respir Cell Mol Biol 2009; 41:290-6.

Kozawa O, Hatakeyama D, Uematsu T. Divergent regulation by p44/p42 MAP kinase and p38 MAP kinase of bone morphogenetic protein-4-stimulated osteocalcin synthesis in osteoblasts. J Cell Biochem 2002; 84:583-9.

Laird D J, von Andrian U H, Wagers A J. Stem cell trafficking in tissue development, growth, and disease. Cell 2008; 132:612-30.

Levy O, Dvir T, Tsur-Gang O, Granot Y, Cohen S. Signal transducer and activator of transcription 3-A key molecular switch for human mesenchymal stem cell proliferation. Int J Biochem Cell Biol 2008; 40:2606-18.

Levy O, Ruvinov E, Reem T, Granot Y, Cohen S. Highly efficient osteogenic differentiation of human mesenchymal stem cells by eradication of STAT3 signaling. Int J Biochem Cell Biol 2010; 42:1823-30.

Marcacci M, Berruto M, Brocchetta D, Delcogliano A, Ghinelli D, Gobbi A, et al. Articular cartilage engineering with Hyalograft C: 3-year clinical results. Clin Orthop Relat Res 2005:96-105.

Nixon A J, Fortier L A, Williams J, Mohammed H. Enhanced repair of extensive articular defects by insulin-like growth factor-I-laden fibrin composites. J Orthop Res 1999; 17:475-87.

Prockop D J. Repair of tissues by adult stem/progenitor cells (MSCs): controversies, myths, and changing paradigms. Mol Ther 2009; 17:939-46.

Qi H, Aguiar D J, Williams S M, La Pean A, Pan W, Verfaillie C M. Identification of genes responsible for osteoblast differentiation from human mesodermal progenitor cells. Proc Natl Acad Sci USA 2003; 100:3305-10.

Re'em T, Kaminer-Israeli Y, Ruvinov E, Cohen S. Chondrogenesis of hMSC in affinity-bound TGF-beta scaffolds. Biomaterials 2012; 33:751-61.

Ruvinov E, Leor J, Cohen S. The effects of controlled HGF delivery from an affinity-binding alginate biomaterial on angiogenesis and blood perfusion in a hindlimb ischemia model. Biomaterials 2010; 31:4573-82.

Ruvinov E, Leor J, Cohen S. The promotion of myocardial repair by the sequential delivery of IGF-1 and HGF from an injectable alginate biomaterial in a model of acute myocardial infarction. Biomaterials 2011; 32:565-78.

Schaefer D, Martin I, Jundt G, Seidel J, Heberer M, Grodzinsky A, et al. Tissue-engineered composites for the repair of large osteochondral defects. Arthritis Rheum 2002; 46:2524-34.

Shao X X, Hutmacher D W, Ho S T, Goh J C, Lee E H. Evaluation of a hybrid scaffold/cell construct in repair of high-load-bearing osteochondral defects in rabbits. Biomaterials 2006; 27:1071-80.

Shapiro L, Cohen S. Novel alginate sponges for cell culture and transplantation. Biomaterials 1997; 18:583-90.

The invention claimed is:

1. A method for constructing a multi-compartment hydrogel comprising the steps of:
   (i) mixing a sulfated polysaccharide and at least one bioactive polypeptide capable of binding said sulfated polysaccharide, thereby forming a bioconjugate;
   (ii) mixing said bioconjugate of (i) with a material capable of forming a hydrogel, thereby forming a composite material comprising said bioconjugate;
   (iii) applying said composite material comprising said bioconjugate of (ii) to a scaffold and optionally adding a hydrogel inducer, thereby forming a hydrogel compartment in said scaffold; and
   (iv) repeating steps (i) to (iii) until the desired number of hydrogel compartments is obtained, wherein each time that step (i) is repeated, the bioconjugate formed in (i) comprises at least one different bioactive peptide and is therefore distinct from each one of the previously obtained bioconjugates, and each new hydrogel compartment formed in (iii) is in contact with at least one of the previously formed hydrogel compartments, thereby forming a multi-compartment hydrogel in said scaffold.

2. A multi-compartment hydrogel obtained by a method comprising the steps of:
   (i) mixing a sulfated polysaccharide and at least one bioactive polypeptide capable of binding said sulfated polysaccharide, thereby forming a bioconjugate;
   (ii) mixing said bioconjugate of (i) with a material capable of forming a hydrogel, thereby forming a composite material comprising said bioconjugate;
   (iii) applying said composite material comprising the bioconjugate of (ii) to a scaffold and optionally adding a hydrogel inducer, thereby forming a hydrogel compartment in said scaffold; and
   (iv) repeating steps (i) to (iii) until the desired number of hydrogel compartments is obtained, wherein each time that step (i) is repeated, the bioconjugate formed in (i) comprises at least one different bioactive peptide and is therefore distinct from each one of the previously obtained bioconjugates, and each new hydrogel compartment formed in (iii) is in contact with at least one of the previously formed hydrogel compartments, thereby forming a multi-compartment hydrogel in said scaffold.

3. The multi-compartment hydrogel of claim 2, having two compartments, wherein the first compartment comprises a bioconjugate of alginate sulfate and TGFβ1, and the second compartment comprises a bioconjugate of alginate sulfate and BMP-4.

4. A kit for use in repair or regeneration of a damaged tissue in a mammal, wherein said kit comprises components for constructing a multi-compartment hydrogel, wherein each compartment comprises a bioconjugate comprising a sulfated polysaccharide and at least one different bioactive peptide, said bioconjugate is therefore distinct from each one of the other bioconjugates, and each hydrogel compartment is in contact with at least one of the other hydrogel compartments, said kit comprising:
   (i) containers comprising components for forming at least two bioconjugates, wherein said components comprise a sulfated polysaccharide and at least two bioactive polypeptides capable of binding said sulfated polysaccharide;
(ii) a container comprising a material capable of forming a hydrogel;
(iii) optionally a scaffold;
(iv) optionally a container comprising a hydrogel inducer; and
(v) instructions for constructing a multi-compartment hydrogel in a scaffold according to claim 2.

5. The kit of claim 4, wherein:
(i) said sulfated polysaccharide and said bioactive polypeptides are each contained separately;
(ii) said sulfated polysaccharide is contained with at least one of said bioactive polypeptides; or
(iii) at least two of said bioactive polypeptides are contained together.

6. The kit of claim 5, wherein said multi-compartment hydrogel is constructed in a void in a damaged tissue in said mammal.

7. The multi-compartment hydrogel of claim 2, wherein said sulfated polysaccharide contains uronic acid residues.

8. The multi-compartment hydrogel of claim 7, wherein the sulfated polysaccharide is alginate sulfate or hyaluronan sulfate.

9. The multi-compartment hydrogel of claim 2, wherein said at least one bioactive polypeptide is a positively-charged polypeptide and/or a heparin-binding polypeptide.

10. The multi-compartment hydrogel of claim 9, wherein said at least one bioactive polypeptide is selected from TGFβ1, a BMP such as BMP-2, 4 or 7, aFGF, PDGF-BB, PDGF-AA, VEGF, IL-6, TPO, SDF, HGF, EGF, IGF-1, bFGF or VEGF.

11. The multi-compartment hydrogel of claim 2, wherein said binding is reversible non-covalent binding involving ionic bonds, electrostatic interactions, hydrophobic interactions, hydrogen bonds or van der Waals forces.

12. The multi-compartment hydrogel of claim 2, wherein said material capable of forming a hydrogel is selected from alginate, a partially calcium cross-linked alginate solution, chitosan or viscous hyaluronan.

13. The multi-compartment hydrogel of claim 2, wherein the multi-compartment hydrogel allows migration and penetration of cells into the multi-compartment hydrogel and interaction of said cells with said at least one bioactive polypeptide.

14. The multi-compartment hydrogel of claim 2, wherein said multi-compartment hydrogel is acellular.

15. The multi-compartment hydrogel of claim 2, wherein step (ii) further comprises mixing said bioconjugate of (i) and said material capable of forming a hydrogel with stem cells, thereby forming a composite material comprising the bioconjugate and stem cells.

16. The multi-compartment hydrogel of claim 2, wherein said scaffold is a void in a damaged tissue in a mammal.

17. The multi-compartment hydrogel of claim 2, wherein said scaffold is a synthetic or artificial mold.

18. The multi-compartment hydrogel of claim 16, wherein said damaged tissue is selected from cartilage, bone tissue, or a combination thereof.

19. The method of claim 1, wherein said sulfated polysaccharide comprises uronic acid residues.

20. The method of claim 19, wherein said polysaccharide is alginate sulfate or hyaluronan sulfate.

21. The method of claim 20, wherein said at least on bioactive polypeptide is a positively-charged polypeptide and/or a heparin-binding polypeptide.

22. The method of claim 21, wherein said at least one bioactive polypeptide is selected from TGFβ1, a BMP such as BMP-2, 4 or 7, aFGF, PDGF-BB, PDGF-AA, VEGF, IL-6, TPO, SDF, HGF, EGF, IGF-1, bFGF or VEGF.

23. The method of claim 1, wherein said desired number of hydrogel compartments comprises two compartments, and wherein the first compartment comprises a bioconjugate of alginate sulfate and TGFβ1, and the second compartment comprises a bioconjugate of alginate sulfate and BMP-4.

24. The method of claim 1, wherein said binding is reversible non-covalent binding involving ionic bonds, electrostatic interactions, hydrophobic interactions, hydrogen bonds or van der Waals forces.

25. The method of claim 1, wherein said material capable of forming a hydrogel is selected from alginate, a partially calcium cross-linked alginate solution, chitosan or viscous hyaluronan.

26. The method of claim 1, wherein said multi-compartment hydrogel allows migration and penetration of cells into the multi-compartment hydrogel and interaction of said cells with said at least one bioactive polypeptide.

27. The method of claim 1, wherein said multi-compartment hydrogel is acellular.

28. The method of claim 1, wherein step (ii) further comprises mixing said bioconjugate of (i) and said material capable of forming a hydrogel with stem cells, thereby forming a composite material comprising said bioconjugate and said stem cells.

29. The method of claim 1, wherein said scaffold is a void in a damaged tissue in a mammal.

30. The method of claim 29, wherein said damaged tissue is selected from cartilage, bone tissue, or a combination thereof.

31. The method of claim 1, wherein said scaffold is a synthetic or artificial mold.

32. A method for the repair or regeneration of a damaged tissue in a mammal, comprising implanting the multi-compartment hydrogel of claim 2 in a void in said tissue.

33. The method of claim 32, for regeneration of articular cartilage and/or woven bone.

34. The method of claim 32, for repair of a subchondral defect.

\* \* \* \* \*